Figure 3:
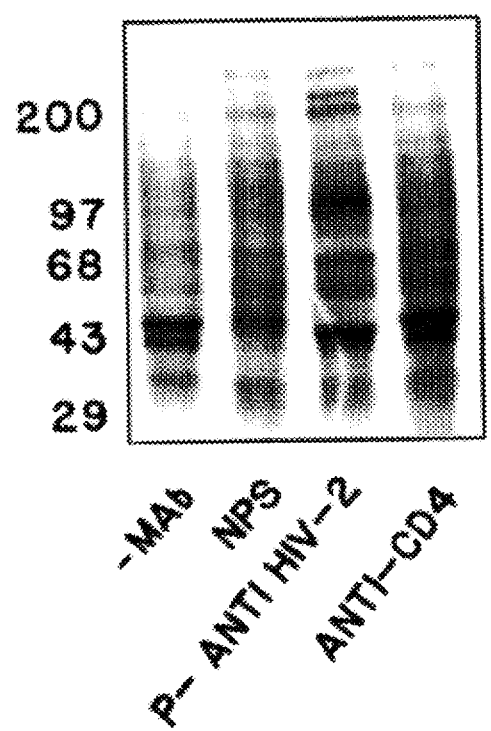
Figure 4:
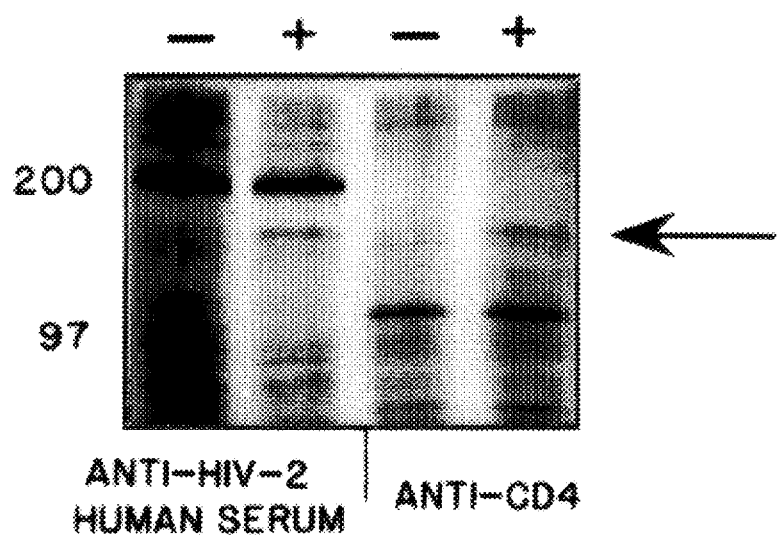

United States Patent [19]

Weiner et al.

[11] Patent Number: 5,714,316
[45] Date of Patent: Feb. 3, 1998

[54] CHIMERIC ENVELOPE PROTEINS FOR VIRAL TARGETING

[75] Inventors: David Weiner, Penn Wynn Hills; William Williams, Havertown; David N. Levy, Philadelphia, all of Pa.

[73] Assignees: The Wistar Institute of Anatomy & Biology; The Trustees of the University of Pennsylvania, both of Philadelphia, Pa.

[21] Appl. No.: 147,890

[22] Filed: Nov. 4, 1993

Related U.S. Application Data

[63] Continuation-in-part of Ser. No. 718,537, Jun. 21, 1991, abandoned.

[51] Int. Cl.$^6$ .............................. C12Q 1/68; C12Q 1/70; C07H 21/02; C12N 15/00
[52] U.S. Cl. .............................. 435/6; 435/5; 435/320.1; 435/240.1; 435/240.2; 435/69.1; 435/69.7; 536/23.1; 536/23.4
[58] Field of Search .............................. 536/23.1, 23.4; 435/320.1, 240.1, 240.2, 5, 69.1, 69.7, 6

[56] References Cited

U.S. PATENT DOCUMENTS

4,593,002  6/1986  Dulbecco .............................. 435/172.3

FOREIGN PATENT DOCUMENTS

| | | |
|---|---|---|
| 0 334 301 A1 | 9/1989 | European Pat. Off. . |
| 0334301 | 9/1989 | European Pat. Off. . |
| WO89/09271 | 10/1989 | WIPO . |
| WO90/12087 | 10/1990 | WIPO . |
| WO91/02554 | 3/1991 | WIPO . |
| WO91/02805 | 3/1991 | WIPO . |
| WO92/07943 | 5/1992 | WIPO . |
| WO93/00103 | 1/1993 | WIPO . |
| WO94/12626 | 6/1994 | WIPO . |

OTHER PUBLICATIONS

R. Tellier et al. (1985) Nature 318:414.
L. A. Lasky et al. (1987) Cell 50:975–985.
A. W. Nienhuis et al. (1991) Cancer 67:2700–2704.
E. O. Freed et al (1990) Proc. Natl. Acad. Sci. USA 87:4650–4654.
S. A. Cannistra et al (1990) Proc. Natl. Acad. Sci. USA 87:93–97.
Cleland, In Protein Folding:In Vivo and In Vitro, ACS, Washington, D.C., CH 1 and CH 19, 1993.
Tellier et al. Nature 318: 414, 1985.
Laskey et al. Cell 50: 975–985, 1987.
Freed et al. PNAS 87: 4650–4654, 1990.
Guitierrez et al. The Lancet 339: 715–721, 1992.
Orkin et al. Report and Recommendations of the PAnel to Assess the NIH Investmetn in Research on Gene Therapy (volume not relevant), 1995.
N. Kasahara et al, "Tissue-Specific Targeting of Retroviral Vectors Through Ligand-Receptor Interactions", Science, 266:1373–1376 (Nov. 25, 1994).
T-H. Chu et al, "Retroviral Vector Particles Displaying the Antigen-Binding Site of an Antibody Enable Cell-Type-Specific Gene Transfer", J. Virol., 69(4):2659–2663 (Apr., 1995).
P. Correll et al, "Expression of Human Glucocerebrosidase in Long-Term Reconstituted Mice Following Retroviral-Mediated Gene Transfer into Hematopoietic Stem Cells", Human Gene Therapy, 1:277–287 (1990).
J. Wilson et al, "Expression of Human Adenosine Deaminase in Mice Reconstituted with Retrovirus-Transduced Hematopoietic Stem Cells", Proc. Natl. Acad. Sci. USA, 87:439–443 (Jan., 1990).
O. Danos et al, "Safe and Efficient Generation of Recombinant Retroviruses with Amphotropic and Ecotropic Host Ranges", Proc. Natl. Acad. Sci. USA, 85:6460–6464 (Sep., 1988).
J. Young et al, "Efficient Incorporation of Human CD4 Protein in Avian Leukosis Virus Particles", Science, 250:1421–1423 (Dec. 7, 1990).

*Primary Examiner*—W. Gary Jones
*Assistant Examiner*—Dianne Rees
*Attorney, Agent, or Firm*—Howson and Howson

[57] ABSTRACT

The present invention provides compositions and methods for targeting recombinant retroviral particles specifically to cells of interest for delivery of desired therapeutic or toxic agents. The invention provides chimeric nucleotide constructs, chimeric proteins formed of a selected viral envelope gene from which a selected sequence has been deleted and into which has been inserted all or an effective portion of a heterologous ligand, said ligand or portion thereof capable of binding to a selected receptor, recombinant viral particles formed of the chimeric proteins, a biological mediator for delivery to the target cell; and retroviral gag and pol proteins. The lack of retroviral nucleic acid renders the viral particle replication defective and non-pathogenic.

11 Claims, 12 Drawing Sheets

FIG. 1

PRIMERS FOR ROD ENV-CD4 CHIMERAS

| | | |
|---|---|---|
| A. | GGCTGCctcgagCAAGGGGCTCGGGAT<u>ATG</u> | 5' HIV-2 ROD XhoI, REV ATG |
| B. | CD4: CTTCTGGGAAGCTGT/GCA/GTTAGTCCACATGTA :env | 3' HIV-2 ROD WITH CD4 TAG |
| C. | /TGT/ACAGCTTCCCAGAAG | 5' CD4 FIRST CYSTEINE |
| D. | /ACA/GATGTAAGTATC | 3' CD4 SECOND CYSTEINE – 1 LOOP |
| E. | /GCA/TGTCCAGGTGCC | 3' CD4 FOURTH CYSTEINE – 2 LOOPS |
| F. | CD4: GATACTTACATC/TGT/AACTCAACAGTAACC :env | 5' HIV-2 ROD WITH CD4 TAG – 1 LOOP |
| G. | CD4: GGCACCTGGACA/TGC/AACTCAACAGTAAC :env | 5' HIV-2 ROD WITH CD4 TAG – 2 LOOPS |
| H. | GCTAGCtctagaACTGCCGTCCC<u>TCA</u>CAG GAGGCGATTTC | 3' HIV-2 ROD XbaI, ENV STOP |

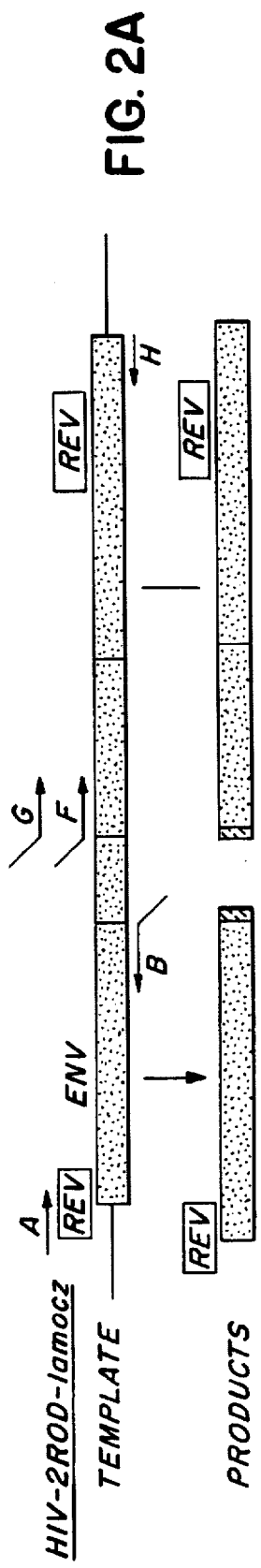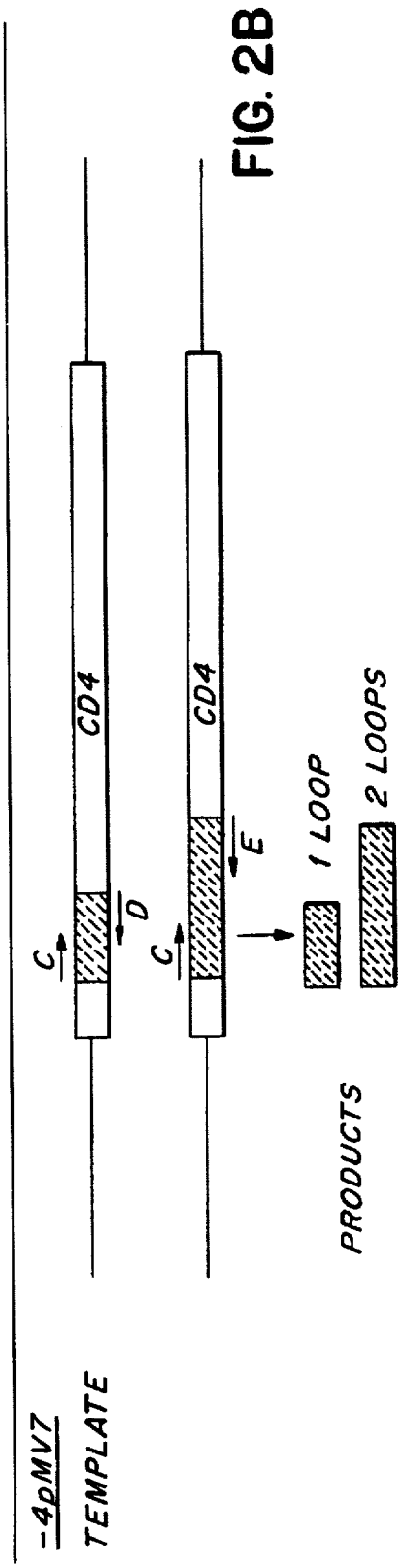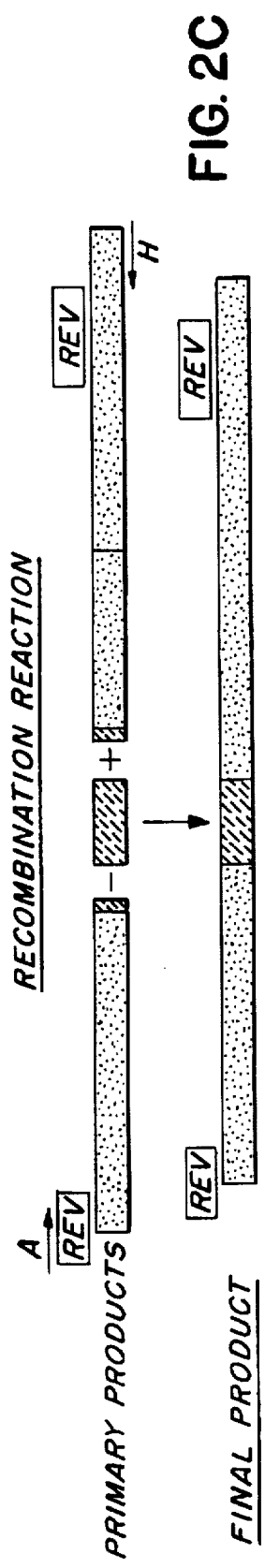

FIG. 5A nucleotide sequence of the GMCSF/HIV-1 chimeric
[SEQ ID NO: 1]

| | | | | |
|---|---|---|---|---|
| CCTTAGCTCG | AGCCTATGGC | AGGAAGAAGC | GGAGACAGCG | ACGAAGAGCT | 50 |
| CATCAGAACA | GTCAGACTCA | TCAAGCTTCT | CTATCAAAGC | AGTAAGTAGT | 100 |
| ACATGTAACG | CAACCTATAC | AATAGTAGC | AATAGTAGCA | TTAGTAGTAG | 150 |
| CAATAATAAT | AGCAATAGTT | GTGTGGTCCA | TAGTAATCAT | AGAATATAGG | 200 |
| AAAATATTAA | GACAAAGAAA | AATAGACAGG | TTAATTGATA | GACTAATAGA | 250 |
| AAGAGCAGAA | GACAGTGGCA | ATGAGAGTGA | AGGAGAAATA | TCAGCACTTG | 300 |
| TGGAGATGGG | GGTGGAGATG | GGGCACCATG | CTCCTTGGGA | TGTTGATGAT | 350 |
| CTGTAGTGCT | ACAGAAAAAT | TGTGGGTCAC | AGTCTATTAT | GGGGTACCTG | 400 |
| TGTGGAAGGA | AGCAACCACC | ACTCTATTTT | GTGCATCAGA | TGCTAAAGCA | 450 |
| TATGATACAG | AGGTACATAA | TGTTTGGGCC | ACACATGCCT | GTGTACCCAC | 500 |
| AGACCCCAAC | CCACAAGAAG | TAGTATTGGT | AAATGTGACA | GAAAATTTTA | 550 |
| ACATGTGGAA | AAATGACATG | GTAGAACAGA | TGCATGAGGA | TATAATCAGT | 600 |
| TTATGGGATC | AAAGCCTAAA | GCCATGTGTA | AAATTAACCC | CACTCTGTGT | 650 |
| TAGTTTAAAG | TGCACTGATT | TGAAGAATGA | TACTAATACC | AATAGTAGTA | 700 |
| GCGGGAGAAT | GATAATGGAG | AAAGGAGAGA | TAAAAAACTG | CTCTTTCAAT | 750 |
| ATCAGCACAA | GCATAAGAGG | TAAGGTGCAG | AAAGAATATG | CATTTTTTTA | 800 |
| TAAACTTGAT | ATAATACCAA | TAGATAATGA | TACTACCAGC | TATAAGTTGA | 850 |
| CAAGTTGTAA | CACCTCAGTC | ATTACACAGG | CCTGTCCAAA | GGTATCCTTT | 900 |
| GAGCCAATTC | CCATACATTA | TTGTGCCCCG | GCTGGTTTTG | CGATTCTAAA | 950 |
| ATGTAATAAT | AAGACGTTCA | ATGGAACAGG | ACCATGTACA | AATGTCAGCA | 1000 |
| CAGTACAATG | TACACATGGA | ATTAGGCCAG | TAGTATCAAC | TCAACTGCTG | 1050 |
| TTAAATGGCA | GTCTAGCAGA | AGAAGAGGTA | GTAATTAGAT | CTGTCAATTT | 1100 |
| CACGGACAAT | GCTAAAACCA | TAATAGTACA | GCTGAACACA | TCTGTAGAAA | 1150 |
| TTAATTGTAC | AAGACCCAAC | AACAATACAA | GAAAAAGAAT | CCGTATCCAG | 1200 |
| AGAGGACCAG | GGAGAGCATT | TGTTACAATA | GGAAAAATAG | GAAATATGAG | 1250 |
| ACAAGCACAT | TGTAACATTA | GTAGAGCAAA | ATGGAATAAC | CAGCCCTGGG | 1300 |

FIG. 5B

```
AGCATGTGAA TGCCATCCAG GAGGCCCGGC GTCTCCTGAA CCTGAGTAGA    1350
GACACTGCTG CTGAGATGAA TGAAACAGTA GAAGTCATCT CAGAAATGTT    1400
TGACCTCCAG GAGCCGACCT GCCTACAGAC CCGCCTGGAG CTGTACAAGC    1450
AGGGCCTGCG GGGCAGCCTC ACCAAGCTCA AGGGCCCCTT GACCATGATG    1500
GCCAGCCACT ACAAGCAGCA CTGCCCTCCA ACCCCGGAAA CTTCCTGTGC    1550
AACCCAGATT ATCACCTTTG AAAGTTTCAA AGAGAACCTG AAGGACTTTC    1600
TGCTTGTCAT CCCCTTTGAC TGCTGGAGC CAGTCCAGGA GGCAGTGGGA    1650
ATAGGAGCTT TGTTCCTTGG GTTCTTGGGA GCAGCAGGAA GCACTATGGG    1700
CGCAGCGTCA ATGACGCTGA CGGTACAGGC CAGACAATTA TTGTCTGGTA    1750
TAGTGCAGCA GCAGAACAAT TTGCTGAGGG CTATTGAGGC GCAACAGCAT    1800
CTGTTGCAAC TCACAGTCTG GGGCATCAAG CAGCTCCAGG CAAGAATCCT    1850
GGCTGTGGAA AGATACCTAA AGGATCAACA GCTCCTGGGG ATTTGGGGTT    1900
GCTCTGGAAA ACTCATTTGC ACCACTGCTG TGCCTTGGAA TGCTAGTTGG    1950
AGTAATAAAT CTCTGGAACA GATTTGGAAT CACACGACCT GGATGGAGTG    2000
GGACAGAGAA ATTAACAATT ACACAAGCTT AATACACTCC TTAATTGAAG    2050
AATCGCAAAA CCAGCAAGAA AAGAATGAAC AAGAATTATT GGAATTAGAT    2100
AAATGGGCAA GTTTGTGGAA TTGGTTTAAC ATAACAAATT GGCTGTGGTA    2150
TATAAAATTA TTCATAATGA TAGTAGGAGG CTTGGTAGGT TTAAGAATAG    2200
TTTTTGCTGT ACTTTCTATA GTGAATAGAG TTAGGCAGGG ATATTCACCA    2250
TTATCGTTTC AGACCCACCT CCCAACCCCG AGGGGACCCG ACAGGCCCGA    2300
AGGAATAGAA GAAGAAGGTG GAGAGAGAGA CAGAGACAGA TCCATTCGAT    2350
TAGTGAACGG ATCCTTGGCA CTTATCTGGG ACGATCTGCG GAGCCTGTGC    2400
CTCTTCAGCT ACCACCGCTT GAGAGACTTA CTCTTGATTG TAACGAGGAT    2450
TGTGGAACTT CTGGGACGCA GGGGGTGGGA AGCCCTCAAA TATTGGTGGA    2500
ATCTCCTACA GTATTGGAGT CAGGAACTAA AGAATAGTGC TGTTAGCTTG    2550
CTCAATGCCA CAGCCATAGC AGTAGCTGAG GGGACAGATA GGGTTATAGA    2600
AGTAGTACAA GGAGCTTGTA GAGCTATTCG CCACATACCT AGAAGAATAA    2650
GACAGGGCTT GGAAAGGATT TTGCTATAAG ATTCTAGACA AGTG    2694
```

FIG. 6A nucleotide sequence of the HIV-1/CD4 chimeric
[SEQ ID NO: 2]:

| | | | | | |
|---|---|---|---|---|---:|
| CCTTAGCTCG | AGCCTATGGC | AGGAAGAAGC | GGAGACAGCG | ACGAAGAGCT | 50 |
| CATCAGAACA | GTCAGACTCA | TCAAGCTTCT | CTATCAAAGC | AGTAAGTAGT | 100 |
| ACATGTAACG | CAACCTATAC | CAATAGTAGC | AATAGTAGCA | TTAGTAGTAG | 150 |
| CAATAATAAT | AGCAATAGTT | GTGTGGTCCA | TAGTAATCAT | AGAATATAGG | 200 |
| AAAATATTAA | GACAAAGAAA | AATAGACAGG | TTAATTGATA | GACTAATAGA | 250 |
| AAGAGCAGAA | GACAGTGGCA | ATGAGAGTGA | AGGAGAAATA | TCAGCACTTG | 300 |
| TGGAGATGGG | GGTGGAGATG | GGGCACCATG | CTCCTTGGGA | TGTTGATGAT | 350 |
| CTGTAGTGCT | ACAGAAAAAT | TGTGGGTCAC | AGTCTATTAT | GGGGTACCTG | 400 |
| TGTGGAAGGA | AGCAACCACC | ACTCTATTTT | GTGCATCAGA | TGCTAAAGCA | 450 |
| TATGATACAG | AGGTACATAA | TGTTTGGGCC | ACACATGCCT | GTGTACCCAC | 500 |
| AGACCCCAAC | CCACAAGAAG | TAGTATTGGT | AAATGTGACA | GAAAATTTTA | 550 |
| ACATGTGGAA | AAATGACATG | GTAGAACAGA | TGCATGAGGA | TATAATCAGT | 600 |
| TTATGGGATC | AAAGCCTAAA | GCCATGTGTA | AAATTAACCC | CACTCTGTGT | 650 |
| TAGTTTAAAG | TGCACTGATT | TGAAGAATGA | TACTAATACC | AATAGTAGTA | 700 |
| GCGGGAGAAT | GATAATGGAG | AAAGGAGAGA | TAAAAAACTG | CTCTTTCAAT | 750 |
| ATCAGCACAA | GCATAAGAGG | TAAGGTGCAG | AAAGAATATG | CATTTTTTA | 800 |
| TAAACTTGAT | ATAATACCAA | TAGATAATGA | TACTACCAGC | TATAAGTTGA | 850 |
| CAAGTTGTAA | CACCTCAGTC | ATTACACAGG | CCTGTCCAAA | GGTATCCTTT | 900 |
| GAGCCAATTC | CCATACATTA | TTGTGCCCCG | GCTGGTTTTG | CGATTCTAAA | 950 |
| ATGTAATAAT | AAGACGTTCA | ATGGAACAGG | ACCATGTACA | AATGTCAGCA | 1000 |
| CAGTACAATG | TACACATGGA | ATTAGGCCAG | TAGTATCAAC | TCAACTGCTG | 1050 |
| TTAAATGGCA | GTCTAGCAGA | AGAAGAGGTA | GTAATTAGAT | CTGTCAATTT | 1100 |
| CACGGACAAT | GCTAAAACCA | TAATAGTACA | GCTGAACACA | TCTGTAGAAA | 1150 |
| TTAATTGTAC | AAGACCCAAC | AACAATACAA | GAAAAGAAT | CCGTATCCAG | 1200 |
| AGAGGACCAG | GGAGAGCATT | TGTTACAATA | GGAAAAATAG | GAAATATGAG | 1250 |
| ACAAGCACAT | TGTAACATTA | GTAGAGCAAA | ATGGAATAAC | ACTTTAAAAC | 1300 |

FIG. 6B

| | | | | | |
|---|---|---|---|---|---|
| AGATAGCTAG | CAAATTAAGA | GAACAATTTG | GAAATAATAA | AACAATAATC | 1350 |
| TTTAAGCAAT | CCTCAGGAGG | GGACCCAGAA | ATTGTAACGC | ACAGTTTTAA | 1400 |
| TTGTACAGCT | TCCCAGAAGA | AGAGCATACA | ATTCCACTGG | AAAAACTCCA | 1450 |
| ACCAGATAAA | GATTCTGGGA | AATCAGGGCT | CCTTCTTAAC | TAAAGGTCCA | 1500 |
| TCCAAGCTGA | ATGATCGCGC | TGACTCAAGA | AGAAGCCTTT | GGGACCAAGG | 1550 |
| AAACTTCCCC | CTGATCATCA | AGAATCTTAA | GATAGAAGAC | TCAGATACTT | 1600 |
| ACATCTGTGA | AGTGGAGGAC | CAGAAGGAGG | AGGTGCAATT | GCTAGTGTTC | 1650 |
| GGATTGACTG | CCAACTCTGA | CACCCACCTG | CTTCAGGGGC | AGAGCCTGAC | 1700 |
| CCTGACCTTG | GAGAGCCCCC | CTGGTAGTAG | CCCCTCAGTG | CAATGTAGGA | 1750 |
| GTCCAAGGGG | TAAAAACATA | CAGGGGGGGA | AGACCCTCTC | CGTGTCTCAG | 1800 |
| CTGGAGCTCC | AGGATAGTGG | CACCTGGACA | TGCTCATCAA | ATATTACAGG | 1850 |
| GCTGCTATTA | ACAAGAGATG | GTGGTAATAG | CAACAATGAG | TCCGAGATCT | 1900 |
| TCAGACCTGG | AGGAGGAGAT | ATGAGGGACA | ATTGGAGAAG | TGAATTATAT | 1950 |
| AAATATAAAG | TAGTAAAAAT | TGAACCATTA | GGAGTAGCAC | CCACCAAGGC | 2000 |
| AAAGAGAAGA | GTGGTGCAGA | GAGAAAAAAG | AGCAGTGGGA | ATAGGAGCTT | 2050 |
| TGTTCCTTGG | GTTCTTGGGA | GCAGCAGGAA | GCACTATGGG | CGCAGCGTCA | 2100 |
| ATGACGCTGA | CGGTACAGGC | CAGACAATTA | TTGTCTGGTA | TAGTGCAGCA | 2150 |
| GCAGAACAAT | TTGCTGAGGG | CTATTGAGGC | GCAACAGCAT | CTGTTGCAAC | 2200 |
| TCACAGTCTG | GGGCATCAAG | CAGCTCCAGG | CAAGAATCCT | GGCTGTGGAA | 2250 |
| AGATACCTAA | AGGATCAACA | GCTCCTGGGG | ATTTGGGGTT | GCTCTGGAAA | 2300 |
| ACTCATTTGC | ACCACTGCTG | TGCCTTGGAA | TGCTAGTTGG | AGTAATAAAT | 2350 |
| CTCTGGAACA | GATTTGGAAT | CACACGACCT | GGATGGAGTG | GGACAGAGAA | 2400 |
| ATTAACAATT | ACACAAGCTT | AATACACTCC | TTAATTGAAG | AATCGCAAAA | 2450 |
| CCAGCAAGAA | AAGAATGAAC | AAGAATTATT | GGAATTAGAT | AAATGGGCAA | 2500 |
| GTTTGTGGAA | TTGGTTTAAC | ATAACAAATT | GGCTGTGGTA | TATAAAATTA | 2550 |
| TTCATAATGA | TAGTAGGAGG | CTTGGTAGGT | TTAAGAATAG | TTTTTGCTGT | 2600 |

FIG. 6C

| | | | | |
|---|---|---|---|---|
| ACTTTCTATA | GTGAATAGAG | TTAGGCAGGG | ATATTCACCA | TTATCGTTTC | 2650
| AGACCCACCT | CCCAACCCCG | AGGGGACCCG | ACAGGCCCGA | AGGAATAGAA | 2700
| GAAGAAGGTG | GAGAGAGAGA | CAGAGACAGA | TCCATTCGAT | TAGTGAACGG | 2750
| ATCCTTGGCA | CTTATCTGGG | ACGATCTGCG | GAGCCTGTGC | CTCTTCAGCT | 2800
| ACCACCGCTT | GAGAGACTTA | CTCTTGATTG | TAACGAGGAT | TGTGGAACTT | 2850
| CTGGGACGCA | GGGGGTGGGA | AGCCCTCAAA | TATTGGTGGA | ATCTCCTACA | 2900
| GTATTGGAGT | CAGGAACTAA | AGAATAGTGC | TGTTAGCTTG | CTCAATGCCA | 2950
| CAGCCATAGC | AGTAGCTGAG | GGGACAGATA | GGGTTATAGA | AGTAGTACAA | 3000
| GGAGCTTGTA | GAGCTATTCG | CCACATACCT | AGAAGAATAA | GACAGGGCTT | 3050
| GGAAAGGATT | TTGCTATAAG | ATTCTAGACA | AGTG | | 3084

Rendered as list:

```
ACTTTCTATA GTGAATAGAG TTAGGCAGGG ATATTCACCA TTATCGTTTC    2650
AGACCCACCT CCCAACCCCG AGGGGACCCG ACAGGCCCGA AGGAATAGAA    2700
GAAGAAGGTG GAGAGAGAGA CAGAGACAGA TCCATTCGAT TAGTGAACGG    2750
ATCCTTGGCA CTTATCTGGG ACGATCTGCG GAGCCTGTGC CTCTTCAGCT    2800
ACCACCGCTT GAGAGACTTA CTCTTGATTG TAACGAGGAT TGTGGAACTT    2850
CTGGGACGCA GGGGGTGGGA AGCCCTCAAA TATTGGTGGA ATCTCCTACA    2900
GTATTGGAGT CAGGAACTAA AGAATAGTGC TGTTAGCTTG CTCAATGCCA    2950
CAGCCATAGC AGTAGCTGAG GGGACAGATA GGGTTATAGA AGTAGTACAA    3000
GGAGCTTGTA GAGCTATTCG CCACATACCT AGAAGAATAA GACAGGGCTT    3050
GGAAAGGATT TTGCTATAAG ATTCTAGACA AGTG                     3084
```

GAG/POL CODING REGION

TRANSFECTION INTO MAMMALIAN CELL
WITH INTEGRATION INTO GENOMIC DNA
AND STABLE EXPRESSION OF GAG AND POL PROTEINS

EMPTY RETROVIRAL PARTICLE
WITHOUT ENVELOPE OR VIRAL RNA

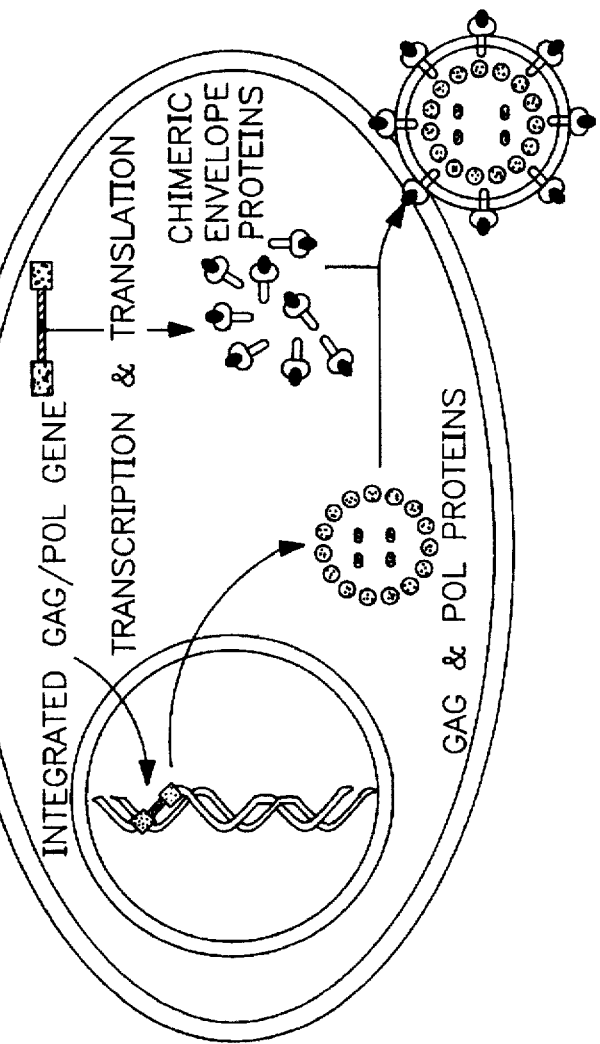
FIG. 8A
FIG. 8B

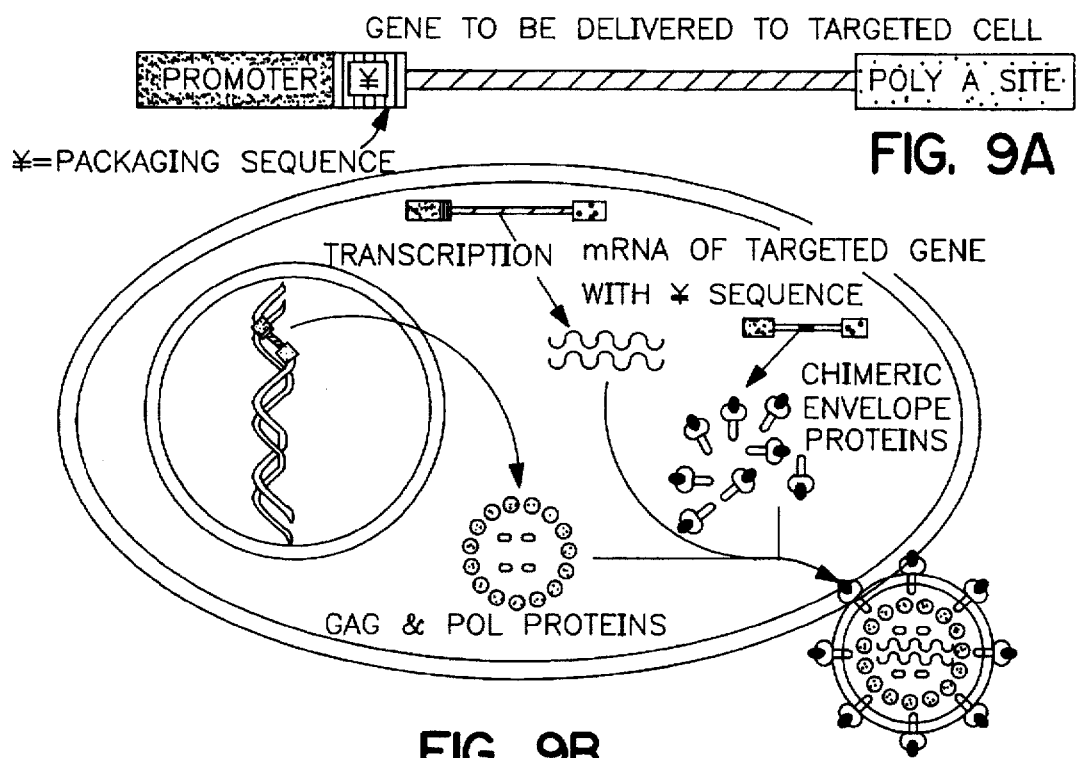
FIG. 9A
FIG. 9B
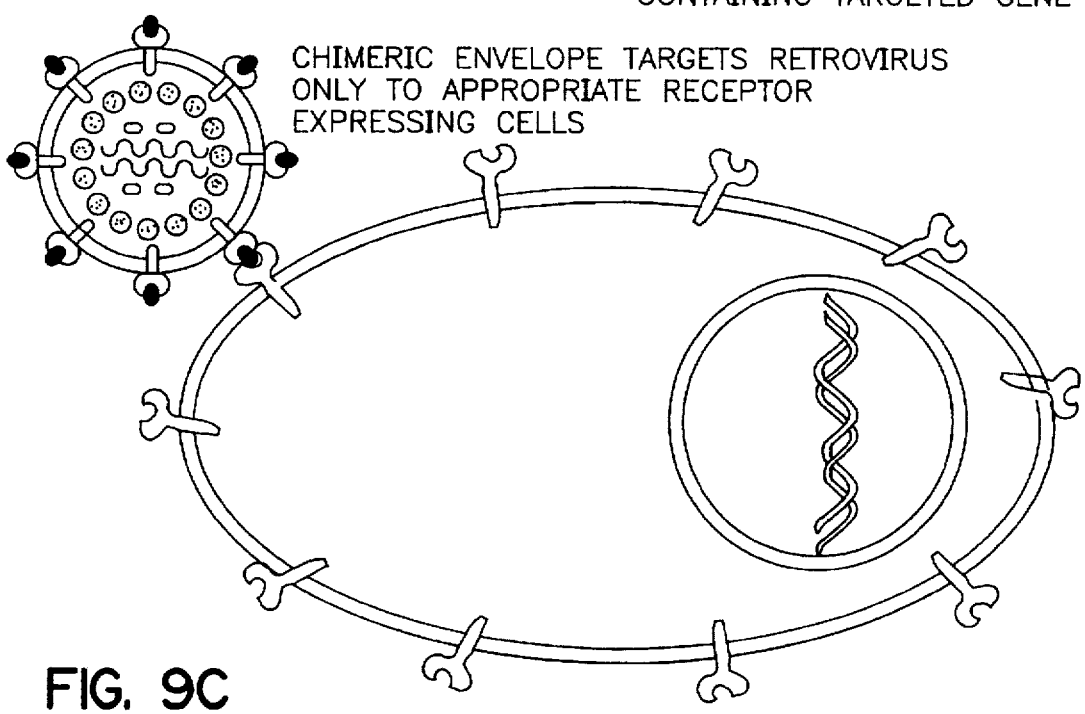
FIG. 9C

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 2694 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:1:

```
CCTTAGCTCG AGCCTATGGC AGGAAGAAGC GGAGACAGCG ACGAAGAGCT CATCAGAACA      60

GTCAGACTCA TCAAGCTTCT CTATCAAAGC AGTAAGTAGT ACATGTAACG CAACCTATAC     120

CAATAGTAGC AATAGTAGCA TTAGTAGTAG CAATAATAAT AGCAATAGTT GTGTGGTCCA     180

TAGTAATCAT AGAATATAGG AAAATATTAA GACAAAGAAA AATAGACAGG TTAATTGATA     240

GACTAATAGA AAGAGCAGAA GACAGTGGCA ATGAGAGTGA AGGAGAAATA TCAGCACTTG     300

TGGAGATGGG GGTGGAGATG GGGCACCATG CTCCTTGGGA TGTTGATGAT CTGTAGTGCT     360

ACAGAAAAAT TGTGGGTCAC AGTCTATTAT GGGGTACCTG TGTGGAAGGA AGCAACCACC     420

ACTCTATTTT GTGCATCAGA TGCTAAAGCA TATGATACAG AGGTACATAA TGTTTGGGCC     480

ACACATGCCT GTGTACCCAC AGACCCCAAC CCACAAGAAG TAGTATTGGT AAATGTGACA     540

GAAAATTTTA ACATGTGGAA AAATGACATG GTAGAACAGA TGCATGAGGA TATAATCAGT     600

TTATGGGATC AAAGCCTAAA GCCATGTGTA AAATTAACCC CACTCTGTGT TAGTTTAAAG     660
```

-continued

| | | | | | |
|---|---|---|---|---|---|
| TGCACTGATT | TGAAGAATGA | TACTAATACC | AATAGTAGTA | GCGGGAGAAT | GATAATGGAG | 720
| AAAGGAGAGA | TAAAAAACTG | CTCTTTCAAT | ATCAGCACAA | GCATAAGAGG | TAAGGTGCAG | 780
| AAAGAATATG | CATTTTTTA | TAAACTTGAT | ATAATACCAA | TAGATAATGA | TACTACCAGC | 840
| TATAAGTTGA | CAAGTTGTAA | CACCTCAGTC | ATTACACAGG | CCTGTCCAAA | GGTATCCTTT | 900
| GAGCCAATTC | CCATACATTA | TTGTGCCCCG | GCTGGTTTTG | CGATTCTAAA | ATGTAATAAT | 960
| AAGACGTTCA | ATGGAACAGG | ACCATGTACA | AATGTCAGCA | CAGTACAATG | TACACATGGA | 1020
| ATTAGGCCAG | TAGTATCAAC | TCAACTGCTG | TTAAATGGCA | GTCTAGCAGA | AGAAGAGGTA | 1080
| GTAATTAGAT | CTGTCAATTT | CACGGACAAT | GCTAAAACCA | TAATAGTACA | GCTGAACACA | 1140
| TCTGTAGAAA | TTAATTGTAC | AAGACCCAAC | AACAATACAA | GAAAAGAAT | CCGTATCCAG | 1200
| AGAGGACCAG | GGAGAGCATT | TGTTACAATA | GGAAAAATAG | GAAATATGAG | ACAAGCACAT | 1260
| TGTAACATTA | GTAGAGCAAA | ATGGAATAAC | CAGCCCTGGG | AGCATGTGAA | TGCCATCCAG | 1320
| GAGGCCCGGC | GTCTCCTGAA | CCTGAGTAGA | GACACTGCTG | CTGAGATGAA | TGAAACAGTA | 1380
| GAAGTCATCT | CAGAAATGTT | TGACCTCCAG | GAGCCGACCT | GCCTACAGAC | CCGCCTGGAG | 1440
| CTGTACAAGC | AGGGCCTGCG | GGCAGCCTC | ACCAAGCTCA | AGGGCCCCTT | GACCATGATG | 1500
| GCCAGCCACT | ACAAGCAGCA | CTGCCCTCCA | ACCCCGGAAA | CTTCCTGTGC | AACCCAGATT | 1560
| ATCACCTTTG | AAAGTTCAA | AGAGAACCTG | AAGGACTTTC | TGCTTGTCAT | CCCCTTTGAC | 1620
| TGCTGGGAGC | CAGTCCAGGA | GGCAGTGGGA | ATAGGAGCTT | TGTTCCTTGG | GTTCTTGGGA | 1680
| GCAGCAGGAA | GCACTATGGG | CGCAGCGTCA | ATGACGCTGA | CGGTACAGGC | CAGACAATTA | 1740
| TTGTCTGGTA | TAGTGCAGCA | GCAGAACAAT | TTGCTGAGGG | CTATTGAGGC | GCAACAGCAT | 1800
| CTGTTGCAAC | TCACAGTCTG | GGCATCAAG | CAGCTCCAGG | CAAGAATCCT | GGCTGTGGAA | 1860
| AGATACCTAA | AGGATCAACA | GCTCCTGGGG | ATTTGGGGTT | GCTCTGGAAA | ACTCATTTGC | 1920
| ACCACTGCTG | TGCCTTGGAA | TGCTAGTTGG | AGTAATAAAT | CTCTGGAACA | GATTTGGAAT | 1980
| CACACGACCT | GGATGGAGTG | GGACAGAGAA | ATTAACAATT | ACACAAGCTT | AATACACTCC | 2040
| TTAATTGAAG | AATCGCAAAA | CCAGCAAGAA | AAGAATGAAC | AAGAATTATT | GGAATTAGAT | 2100
| AAATGGGCAA | GTTTGTGGAA | TTGGTTTAAC | ATAACAAATT | GGCTGTGGTA | TATAAAATTA | 2160
| TTCATAATGA | TAGTAGGAGG | CTTGGTAGGT | TTAAGAATAG | TTTTTGCTGT | ACTTTCTATA | 2220
| GTGAATAGAG | TTAGGCAGGG | ATATTCACCA | TTATCGTTTC | AGACCCACCT | CCCAACCCCG | 2280
| AGGGGACCCG | ACAGGCCCGA | AGGAATAGAA | GAAGAAGGTG | GAGAGAGAGA | CAGAGACAGA | 2340
| TCCATTCGAT | TAGTGAACGG | ATCCTTGGCA | CTTATCTGGG | ACGATCTGCG | GAGCCTGTGC | 2400
| CTCTTCAGCT | ACCACCGCTT | GAGAGACTTA | CTCTTGATTG | TAACGAGGAT | TGTGGAACTT | 2460
| CTGGGACGCA | GGGGGTGGGA | AGCCCTCAAA | TATTGGTGGA | ATCTCCTACA | GTATTGGAGT | 2520
| CAGGAACTAA | AGAATAGTGC | TGTTAGCTTG | CTCAATGCCA | CAGCCATAGC | AGTAGCTGAG | 2580
| GGGACAGATA | GGGTTATAGA | AGTAGTACAA | GGAGCTTGTA | GAGCTATTCG | CCACATACCT | 2640
| AGAAGAATAA | GACAGGGCTT | GGAAAGGATT | TTGCTATAAG | ATTCTAGACA | AGTG | 2694

( 2 ) INFORMATION FOR SEQ ID NO:2:

( i ) SEQUENCE CHARACTERISTICS:
        ( A ) LENGTH: 3084 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:2:

-continued

```
CCTTAGCTCG AGCCTATGGC AGGAAGAAGC GGAGACAGCG ACGAAGAGCT CATCAGAACA      60
GTCAGACTCA TCAAGCTTCT CTATCAAAGC AGTAAGTAGT ACATGTAACG CAACCTATAC     120
CAATAGTAGC AATAGTAGCA TTAGTAGTAG CAATAATAAT AGCAATAGTT GTGTGGTCCA     180
TAGTAATCAT AGAATATAGG AAAATATTAA GACAAGAAA AATAGACAGG TTAATTGATA      240
GACTAATAGA AGAGCAGAA GACAGTGGCA ATGAGAGTGA AGGAGAAATA TCAGCACTTG      300
TGGAGATGGG GGTGGAGATG GGGCACCATG CTCCTTGGGA TGTTGATGAT CTGTAGTGCT     360
ACAGAAAAAT TGTGGGTCAC AGTCTATTAT GGGGTACCTG TGTGGAAGGA AGCAACCACC     420
ACTCTATTTT GTGCATCAGA TGCTAAAGCA TATGATACAG AGGTACATAA TGTTTGGGCC     480
ACACATGCCT GTGTACCCAC AGACCCCAAC CCACAAGAAG TAGTATTGGT AAATGTGACA     540
GAAAATTTTA ACATGTGGAA AAATGACATG GTAGAACAGA TGCATGAGGA TATAATCAGT     600
TTATGGGATC AAAGCCTAAA GCCATGTGTA AAATTAACCC CACTCTGTGT TAGTTTAAAG     660
TGCACTGATT TGAAGAATGA TACTAATACC AATAGTAGTA GCGGGAGAAT GATAATGGAG     720
AAAGGAGAGA TAAAAAACTG CTCTTTCAAT ATCAGCACAA GCATAAGAGG TAAGGTGCAG     780
AAAGAATATG CATTTTTTTA TAAACTTGAT ATAATACCAA TAGATAATGA TACTACCAGC     840
TATAAGTTGA CAAGTTGTAA CACCTCAGTC ATTACACAGG CCTGTCCAAA GGTATCCTTT     900
GAGCCAATTC CCATACATTA TTGTGCCCCG GCTGGTTTTG CGATTCTAAA ATGTAATAAT     960
AAGACGTTCA ATGGAACAGG ACCATGTACA AATGTCAGCA CAGTACAATG TACACATGGA    1020
ATTAGGCCAG TAGTATCAAC TCAACTGCTG TTAAATGGCA GTCTAGCAGA AGAAGAGGTA    1080
GTAATTAGAT CTGTCAATTT CACGGACAAT GCTAAAACCA TAATAGTACA GCTGAACACA    1140
TCTGTAGAAA TTAATTGTAC AAGACCCAAC AACAATACAA GAAAAGAAT CCGTATCCAG     1200
AGAGGACCAG GGAGAGCATT TGTTACAATA GGAAAAATAG GAAATATGAG ACAAGCACAT    1260
TGTAACATTA GTAGAGCAAA ATGGAATAAC ACTTTAAAAC AGATAGCTAG CAAATTAAGA    1320
GAACAATTTG GAAATAATAA AACAATAATC TTTAAGCAAT CCTCAGGAGG GGACCCAGAA    1380
ATTGTAACGC ACAGTTTTAA TTGTACAGCT TCCAGAAGA AGAGCATACA ATTCCACTGG     1440
AAAAACTCCA ACCAGATAAA GATTCTGGGA AATCAGGGCT CCTTCTTAAC TAAAGGTCCA    1500
TCCAAGCTGA ATGATCGCGC TGACTCAAGA AGAAGCCTTT GGGACCAAGG AAACTTCCCC    1560
CTGATCATCA GAATCTTAAA GATAGAAGAC TCAGATACTT ACATCTGTGA AGTGGAGGAC    1620
CAGAAGGAGG AGGTGCAATT GCTAGTGTTC GGATTGACTG CCAACTCTGA CACCCACCTG    1680
CTTCAGGGGC AGAGCCTGAC CCTGACCTTG GAGAGCCCCC TGGTAGTAG CCCCTCAGTG     1740
CAATGTAGGA GTCCAAGGGG TAAAAACATA CAGGGGGGGA AGACCCTCTC CGTGTCTCAG    1800
CTGGAGCTCC AGGATAGTGG CACCTGGACA TGCTCATCAA ATATTACAGG GCTGCTATTA    1860
ACAAGAGATG GTGGTAATAG CAACAATGAG TCCGAGATCT TCAGACCTGG AGGAGGAGAT    1920
ATGAGGGACA ATTGGAGAAG TGAATTATAT AAATATAAAG TAGTAAAAAT TGAACCATTA    1980
GGAGTAGCAC CCACCAAGGC AAAGAGAAGA GTGGTGCAGA GAGAAAAAAG AGCAGTGGGA    2040
ATAGGAGCTT TGTTCCTTGG GTTCTTGGGA GCAGCAGGAA GCACTATGGG CGCAGCGTCA    2100
ATGACGCTGA CGGTACAGGC CAGACAATTA TTGTCTGGTA TAGTGCAGCA GCAGAACAAT    2160
TTGCTGAGGG CTATTGAGGC GCAACAGCAT CTGTTGCAAC TCACAGTCTG GGCATCAAG     2220
CAGCTCCAGG CAAGAATCCT GGCTGTGGAA AGATACCTAA GGATCAACA GCTCCTGGGG     2280
ATTTGGGGTT GCTCTGGAAA ACTCATTTGC ACCACTGCTG TGCCTTGGAA TGCTAGTTGG    2340
AGTAATAAAT CTCTGGAACA GATTTGGAAT CACACGACCT GGATGGAGTG GGACAGAGAA    2400
```

```
ATTAACAATT  ACACAAGCTT  AATACACTCC  TTAATTGAAG  AATCGCAAAA  CCAGCAAGAA    2460

AAGAATGAAC  AAGAATTATT  GGAATTAGAT  AAATGGGCAA  GTTTGTGGAA  TTGGTTTAAC    2520

ATAACAAATT  GGCTGTGGTA  TATAAAATTA  TTCATAATGA  TAGTAGGAGG  CTTGGTAGGT    2580

TTAAGAATAG  TTTTTGCTGT  ACTTTCTATA  GTGAATAGAG  TTAGGCAGGG  ATATTCACCA    2640

TTATCGTTTC  AGACCCACCT  CCCAACCCCG  AGGGGACCCG  ACAGGCCCGA  AGGAATAGAA    2700

GAAGAAGGTG  GAGAGAGAGA  CAGAGACAGA  TCCATTCGAT  TAGTGAACGG  ATCCTTGGCA    2760

CTTATCTGGG  ACGATCTGCG  GAGCCTGTGC  CTCTTCAGCT  ACCACCGCTT  GAGAGACTTA    2820

CTCTTGATTG  TAACGAGGAT  TGTGGAACTT  CTGGGACGCA  GGGGGTGGGA  AGCCCTCAAA    2880

TATTGGTGGA  ATCTCCTACA  GTATTGGAGT  CAGGAACTAA  AGAATAGTGC  TGTTAGCTTG    2940

CTCAATGCCA  CAGCCATAGC  AGTAGCTGAG  GGGACAGATA  GGGTTATAGA  AGTAGTACAA    3000

GGAGCTTGTA  GAGCTATTCG  CCACATACCT  AGAAGAATAA  GACAGGGCTT  GGAAAGGATT    3060

TTGCTATAAG  ATTCTAGACA  AGTG                                             3084
```

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

```
GGCTGCCTCG  AGCAAGGGGC  TCGGGATATG                                         30
```

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:4:

```
CTTCTGGGAA  GCTGTGCAGT  TAGTCCACAT  GTA                                    33
```

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:5:

```
TGTACAGCTT  CCCAGAAG                                                       18
```

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:6:

ACAGATGTAA GTATC                                                                    15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:7:

GCATGTCCAG GTGCC                                                                    15

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:8:

GATACTTACA TCTGTAACTC AACAGTAACC                                                    30

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:9:

GGCACCTGGA CATGCAACTC AACAGTAAC                                                     29

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:10:

GCTAGCTCTA GAACTGCCGT CCCTCACAGG AGGCGATTTC                                         40

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:11:

CCTTAAGCTC GAGCCTATGG CAGGAAGAAG CG                                                 32

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:12:

CACTTGTTCT AGAATCTTAT AGCAAAATCC        30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:13:

ATGCTGCCAG GGCTGGTTAT TCCATTTTGC        30

( 2 ) INFORMATION FOR SEQ ID NO:14:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:14:

GCAAAAATGG AATAACCAGC CCTGGCAGCA T        31

( 2 ) INFORMATION FOR SEQ ID NO:15:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:15:

CTCTTGTTAA TAGCAGCTCC TGGACTGGCT C        31

( 2 ) INFORMATION FOR SEQ ID NO:16:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:16:

GAGCCAGTCC AGGAGCTGCT ATTAACAAGA G        31

( 2 ) INFORMATION FOR SEQ ID NO:17:

( i ) SEQUENCE CHARACTERISTICS:
        ( A ) LENGTH: 17 base pairs (B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:17:

ACAATTAAAA CTGTGCG                        17

(2) INFORMATION FOR SEQ ID NO:18:

(i) SEQUENCE CHARACTERISTICS:
(A) LENGTH: 35 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:18:

CGCACAGTTT TAATTGTACA GCTTCCAGA AGAAG      35

(2) INFORMATION FOR SEQ ID NO:19:

(i) SEQUENCE CHARACTERISTICS:
(A) LENGTH: 34 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:19:

CCTGTAATAT TTGATGAGCA TGTCCAGGTG CCAC      34

(2) INFORMATION FOR SEQ ID NO:20:

(i) SEQUENCE CHARACTERISTICS:
(A) LENGTH: 17 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:20:

TCATCAAATA TTACAGG                        17

CHIMERIC ENVELOPE PROTEINS FOR VIRAL TARGETING

CROSS-REFERENCE TO RELATED APPLICATION

This application is a continuation-in-part of U.S. patent application Ser. No. 07/718,537, filed Jun. 21, 1991 now abandoned.

This invention was made with the financial assistance of a grant from the National Institutes of Health. The U.S. government has certain rights in this invention.

FIELD OF THE INVENTION

The present invention relates generally to the area of delivery of a biological mediator to a cellular target. More specifically the invention discloses recombinant chimeric proteins capable of effecting such delivery.

BACKGROUND OF THE INVENTION

Delivery of a specific biological mediator, e.g., a drug, a toxin, or a gene or gene product, to a specific cellular target in vivo or in vitro requires the very high specificity and efficiency. Viral particles, and in particular retroviruses, continue to be a major focus for use as delivery vehicles for gene therapy or other biological mediators. The natural host ranges of these viruses has historically determined the cellular subsets which may be targeted by such systems.

The construction of chimeric molecules incorporating binding domains from one source and structural and/or effector domains from another has emerged as an important technique to study protein structure and for the development of novel reagents for the diagnosis and/or treatment of disease.

In the case of retroviruses, the host range is determined by the viral envelope proteins, of which there are two: the transmembrane glycoprotein and the external glycoprotein. The external glycoprotein is anchored to the virus or cell surface via a covalent or noncovalent linkage to the transmembrane glycoprotein. Viral binding to the target cell is mediated by the external glycoprotein and this interaction is the major determinant of virus host range within a species.

The envelope proteins of the Human Immunodeficiency Viruses (HIV-1 and HIV-2) confer cell tropism. In nature, the HIV envelope precursor glycoprotein gp160 is cleaved to yield two mature envelope glycoproteins: gp120, the external glycoprotein, and gp41, the transmembrane glycoprotein. The external glycoprotein, gp120, binds the T lymphocyte antigen CD4 and establishes CD4 positive T lymphocytes as a major target for infection in vivo. Other, less well defined, mechanisms also operate in the viral binding of HIV. Bifunctional antibodies incorporating the gp120 binding region of CD4 have allowed the targeting of cytotoxic cells to HIV envelope expressing cells. Soluble CD4 variants incorporating antibody constant regions have shown strong neutralization efficacy in vitro and long half life in vivo.

The sequences of gp160 have been published for HIV-1 and HIV-2. See, for HIV-1 gp160, B. Starchich et al, *Science*, 227:538–540 (1985) and L. Ratner et al, *Nature*, 313:227–284 (1985). For HIV-2, see, F. Clavel et al, *Nature*, 324:691–695 (1986). The HIV envelope precursor protein gp160 in its uncleaved state retains high affinity for CD4. However, cleavage of gp160 into the external envelope protein gp120 and the transmembrane protein gp41 is necessary for the production of mature envelope capable of mediating fusion with CD4+ cells. The primary sequence requirements and structural requirements for processing of gp160 into mature gp120 and gp41 are not well understood. Deletion and single residue substitution analysis of HIV-1 envelope have determined that cleavage of gp160 into gp120 and gp41 can be disrupted by alterations distal to the cleavage site. Alternatively, non-conservative substitutions near the cleavage site between gp120 and gp41 can have negligible effect on cleavage.

The region of gp120 responsible for the interaction with the target of HIV, e.g., CD4, has been defined by antibody blocking and mutagenesis studies. This CD4 binding site is found near the carboxyl terminus of gp120. The region of gp120 to which most of the CD4 binding function has been attributed is flanked by two cysteine residues which are disulfide-linked, forming a loop structure called V4. The actual contact region for CD4, or a major part of it, is believed to reside between amino acids 390 and 407 on HIV-1 HXB2 gp120, a strain provided by the National Institutes of Health, and, by analogy, between amino acids 400 and 419 on HIV-2 ROD gp120 (another commonly used NIH strain). The sequences of both strains are publicly available and known to those of skill in the art. The region surrounding and including this putative CD4 binding domain of HIV-2 ROD has structural similarity with immunoglobulin domains. Direct assignment of function for this region of the external envelope protein has been difficult because of the difficulty in reconstituting CD4 binding using small protein analogs derived from this region.

PCT Patent Application WO91/02805, published Mar. 7, 1991 refers to recombinant retroviruses carrying a vector construct designed to express a selected protein in a target cell. European Patent Application 243,204, refers to the use of retroviral vectors to deliver genes for proteins, such as tumor necrosis factor (TNF).

Construction of a molecule preserving all those attributes necessary for viral infectivity (while perhaps removing those related to cell pathogenesis) will be necessary for the successful development of targeted retroviral vectors. Thus, there remains a need in the art for compositions and methods for delivering a therapeutic or toxic agent or a diagnostic reagent or label to an infected cell to enable treatment and/or diagnosis of viral and other types of disease.

SUMMARY OF THE INVENTION

In one aspect, the present invention provides a chimeric nucleotide construct comprising a nucleotide sequence of a selected viral envelope gene from which a selected sequence, preferably including all or a portion of the native binding region-encoding sequences, has been deleted and into which has been inserted all or an effective portion of a synthetic ligand-encoding nucleotide sequence. The ligand or portion thereof is capable of binding to a selected receptor. The location of the receptor defines the target cell.

In another aspect, the present invention includes a chimeric protein, which comprises a modified retrovital gp160 protein. This protein comprises an intact gp41 transmembrane protein and the external protein gp120 which has been modified by replacing the native retroviral binding site region with a synthetic or artificial ligand. Thus, this chimeric protein is produced by the recombinant expression of the chimeric nucleotide construct.

In another aspect the present invention includes a vector molecule which comprises a chimeric nucleotide construct as described above under the regulatory control of a sequence which is capable of directing the expression of the chimeric protein containing the synthetic ligand in a selected host cell.

In still another aspect, cells transfected with the vector of this invention are provided. Such host cells are preferably mammalian cells, such as COS-7 cells, or insect cells.

In another aspect, the present invention provides a recombinant virus particle comprising the association of an above-described chimeric protein, a retroviral gag protein, a retroviral pol protein, and a biological mediator for delivery to the target cell. By virtue of the deletion of the native retroviral binding region, and thus, the lack of a complete env protein provided by the chimeric protein, the viral particle is incapable of targeting its native ligand receptor. The recombinant viral particle is non-pathogenic and incapable of recombination in vivo into a pathogenic form because it lacks the portion of the env protein responsible for targeting native retroviral cellular receptors and lacks viral nucleic acids.

In still a further aspect, the invention provides a host cell transfected with a vector as described above and also comprising a selected biological mediator, in association with a retrovital packaging sequence and the retroviral gag and pol genes under control of a suitable expression control sequence.

In yet another aspect the invention provides a method for producing a recombinant viral particle of this invention, by culturing under suitable conditions the above described host cell.

Still a further aspect of the present invention is a diagnostic composition comprising the chimeric protein produced by expression of the chimeric construct of this invention.

Further, the invention provides a method for treating a patient for a disease state comprising administering to said patient an effective amount of a recombinant viral particle protein of the present invention, the administration being either in vivo or ex vivo.

Other aspects and advantages of the present invention are described further in the following detailed description of preferred embodiments of the present invention.

BRIEF DESCRIPTION OF THE DRAWINGS

FIG. 1 is an illustration of the sequences [SEQ ID NO: 3–10] involved in the PCR and recombinant construction of embodiments of this invention, as described in Example 2. All primers in this figure are shown 5' to 3'. The slashes (/) depict the locations in the sequence where the recombinational events occur. Note that \TGT\ and \TGC\ indicate codons for Cysteine; and /ACA/ and /GCA/ indicate the reverse complement of Cysteine.

FIG. 2A is an illustration of the construction of the Env-CD4 chimeric molecules described in detail in Examples 1 and 2, which indicates the PCR amplification of the env and rev genes using primers A, B, G, F and H of FIG. 1.

FIG. 2B is an illustration of another priming event using a CD4 template and primers C, D and E of FIG. 1 to produce 1 and 2 loops of CD4.

FIG. 2C illustrates the recombinant reaction producing the chimeric construct.

FIG. 3 is a drawing of the electrophoretic gel indicating the immunoprecipitation of HIV-2 env-CD4 1 loop.

FIG. 4 is a drawing of the electrophoretic gel indicating the immunoprecipitation of HIV-2 env-CD4 2 loop.

FIG. 5 provides the sequences [SEQ ID NO: 1] of the GMCSF/HIV-1 chimeric provided in Example 7.

FIG. 6 provides the sequences [SEQ ID NO: 2) of the HIV-1/CD4 chimeric provided in Example 9.

FIG. 7A illustrates a vector construct for the expression of gag (structural) and pol (polymerase) genes.

FIG. 7B illustrates the transfection of the construct of FIG. 7A into a mammalian cell with integration into genomic DNA.

FIG. 7C illustrates the resulting gag/pol expressing cell line, which following transcription and translation of the integrated gag/pol gene, results in the packaging and expression of an empty retroviral particle without envelope or viral RNA. See Example 10 for details.

FIG. 8A illustrates a vector construct of the invention containing a chimeric envelope coding region, between a promoter and poly A site.

FIG. 8B illustrates transfection of the construct of FIG. 8A into the gag/pol expressing cell line of FIG. 7C, resulting in a targeted packaging cell line which produces an empty retroviral particle with chimeric envelope without viral RNA.

FIG. 9A is an illustration of a vector construct containing a retroviral packaging sequence, a gene to be delivered to the targeted cells and a promoter and polyA site.

FIG. 9B illustrates the transfection of the construction of FIG. 9A into the cell of FIG. 8C wherein the gene to be delivered is transcribed into mRNA with a packaging sequence. The assembly of the gene to be delivered, the packaging sequence, the chimeric envelope protein and the gag and pol proteins result in the production of a retroviral particle with chimeric envelope containing the targeted gene.

FIG. 9C illustrated the targeting of a selected cell by the retroviral particle of FIG. 9B and the binding of the particle to the cell receptor.

DETAILED DESCRIPTION OF THE INVENTION

The present invention provides compositions and methods for delivering a selected biological mediator to only selected target cells by use of a non-pathogenic recombinant viral particle which contains a target host range tailored to a selected cellular subset.

According to the present invention, a recombinant viral particle is produced by modifying the external envelope protein of a selected virus, preferably a retrovirus, in order to direct virus binding and infection to a particular cellular target. Selected cell surface molecules function as novel receptors for infection by the recombinant viral particle of this invention. Infection by the chimeric viral particle is thus specifically directed and restricted to cells displaying these antigens via the interaction of the modified viral envelope with the antigens.

A recombinant viral particle of this invention is produced by the association in a host cell of a chimeric protein, a selected biological modifier and the gag and pol proteins. This association is described in detail below and with resort to the following definitions.

As used herein, a "chimeric construct" or "chimeric nucleotide construct" refers to a modified envelope gene which contains a deletion in the region encoding the native binding region, and into which deletion an artificial or synthetic nucleic acid sequence encoding a non-native ligand or binding region has been inserted. A "binding region" is an epitope on a polypeptide or other amino acid sequence which binds to a selected receptor.

As used herein, a "ligand" is a substance which specifically binds to a receptor. The ligand may be selected from among a wide variety of lymphokines, growth factors, hormones, and viral, bacterial or other proteins having their respective receptors present on mammalian or bacterial cells, or viruses. Selected ligand receptors include antigens involved in defined receptor-ligand interactions. A non-exclusive list of selected ligands includes lymphokines, growth factors, hormones, and viral, bacterial or other proteins. One preferred cytokine ligand is Granulocyte-Macrophage Colony Stimulating Factor (GMCSF) and fragments thereof capable of binding to the GMCSF receptor on pluripotent stem cells. See, e.g. D. Cosman, *Cytokine*, 5(2) :95–102 (March 1993); A. Miyajima, *Int. J. Cell. Cloning*, 19(3):126–134 (May 1992); and J. F. Bazan, *Neuron*, 7(2) :197–208 (August 1991). Specifically, along with GM-CSF, IL-3, IL-5, IL-6, IL-2, G-CSF, prolactin, cholinergic differentiation factor, ciliary neurotrophic factor, and growth hormone are included in this family of cytokines characterized structurally as four helix bundles which interact with receptors containing a conserved pattern of cystein residues and a WSXWS box. Other ligands, including the members of the immunoglobulin supergene family, are known in the art, and may be useful in the present invention. See, e.g., E. A. Kabat et al, "Sequences of proteins of immunological interest", U.S. Department of Health and Human Services (1991), J. P. Johnson, *Cancer Metastasis Rev.*, 10(1):11–22 (May 1991); and M. L. Dustin et al, *Immunol. Today*, 9(7–8):213–215 (July–August 1988). Additionally, other ligands of the cytokine supergene family are known.

Another preferred viral ligand is CD4 and fragments thereof which are capable of binding to its receptor on the gp120 protein of HIV I envelope. Binding sites of external glycoproteins of other retroviruses are known in the art and may be readily selected for similar use in this invention. See, e.g., M. Kowalski et al, *Science*, 237:1351–1355 (1987); A. Cordonnier et al, *Nature*, 340(6234):571–574 (1989); A. Ashkenazi et al, *Proc. Natl. Acad. Sci. USA*, 87(18) :7150–7154 (1990); Wilson et al, *J. Virol.*, 63(5):2374–2378 (1989); and C. Ruegg et al, *J. Virol.*, 63(8):3250–3256 (1989) for discussion of such retroviral ligand regions. The sequences of human GM-CSF and CD4 are provided in Kabat et al, cited above.

A "chimeric protein" is the amino acid sequence encoded by the chimeric construct defined above. This protein may be obtained by recombinant expression of the chimeric nucleotide construct in a suitable host cell.

As used herein, a "recombinant viral particle" refers to a viral particle formed by the expression and operative assembly within a cell of a chimeric protein, a selected biological mediator for delivery to a selected cell under the control of a retroviral packaging gene, and the retroviral gag and pol proteins. Such a recombinant viral particle is useful for diagnostic purposes and/or therapy, depending upon the selected synthetic ligand inserted into the chimeric protein and the biological mediator with which it is associated. These viral particles are non-pathogenic because they lack the portions of the env protein responsible for targeting native retroviral cellular receptors and also lack viral nucleic acids.

A "biological mediator" is the agent intended for delivery to a desired target cell, as defined herein, and may be any desired therapeutic agent, gene product, diagnostic label, and/or a toxic agent. Among such toxic agents include, without limitation, compounds useful to kill the target cell, e.g., ricin. Suitable gene products include, without limitation, those which a cell is lacking, such as in the case of cystic fibrosis, the cystic fibrosis gene or adenosinedeaminase (ADA). Other suitable agents include therapeutic products, such as antibiotics, growth factors, cytokines, antisense nucleotides, dominant negative mutants of pathogenic gene products, polynucleotide drugs, polynucleotide vaccines, antioncogenes, intracellular antibodies, or agents which can bind the receptors of viruses, among others.

As provided by this invention, a chimeric protein is made by recombinantly expressing in a selected host cell a chimeric nucleotide construct comprising a nucleotide sequence of a selected viral envelope gene from which a selected sequence has been deleted. That deleted sequence is preferably all or a portion of the sequence encoding the native targeting region. The construct may be made from any number of viruses having similar envelope protein genes, including vaccinia viruses, and adenoviruses, among others. However, the presently preferred virus for use in this invention is a retrovirus. Most preferably, the virus selected for the preparation of a chimeric construct of this invention is Human Immunodeficiency Virus (HIV), either HIV-1 or HIV-2. The envelope gene in question is preferably gp160 or gp120 or a portion thereof.

All or an effective portion of a synthetic or heterologous ligand-encoding nucleotide sequence is inserted into the construct at the site of the deletion. The incorporation of the whole ligand encoding sequence or a part of it which is known to be sufficient for binding to the receptor, into the virus envelope glycoprotein provides a method for redirecting the binding specificity of the viral envelope protein in the chimeric protein, and hence in the recombinant virus particle, to cells expressing the receptor.

Also present on the chimeric construct according to this invention is a regulatory control sequence capable of directing the expression of the ligand in a selected host cell.

The production of chimeric constructs (FIG. 8A) of this invention employ conventional recombinant DNA technology [see, e.g., Sambrook et al, Molecular Cloning A Laboratory Manual., 2nd edition, Cold Spring Harbor Laboratory, Cold Spring Harbor, N.Y. (1989)]. Briefly described, a chimeric construct of this invention, e.g., the native-ligand-deleted HIV gp120 encoding sequences and the inserted synthetic ligand encoding sequences, are appropriately ligated and desirably cloned into a selected expression vector containing regulatory control sequences suitable for directing the replication and expression of the chimeric protein in a selected host cell. This vector may be selected from among many known vectors suitable for host cell expression. Regulatory sequences include promoter fragments, terminator fragments and other suitable sequences which direct the expression of the protein in an appropriate host cell.

The vector is transfected by conventional means into a host cell, preferably a mammalian or insect cell (e.g. baculovirus) for stable or transient expression. Procedures necessary for the construction and use of recombinant vectors and host cells described below are known to those of skill in the art. See, e.g., Sambrook et al, cited above.

The host cell, which has been transformed with a chimeric construct coding for expression of a chimeric protein under the control of known regulatory sequences, may then be cultured under suitable culture conditions to express the chimeric protein. The resulting chimeric protein comprises viral envelope protein sequences flanking the synthetic ligand, produced by expression of the synthetic ligand-encoding nucleotide sequence of the construct. This synthetic ligand is capable of binding to a selected receptor. The expressed chimeric protein may be recovered, isolated and purified from the culture medium (or from the cell, if expressed intracellularly) by appropriate means known to one of skill in the art for analysis, such as by syncytia formation assays or immunoprecipitation assays to determine its binding abilities, as described in detail below.

With regard to the following discussion of the construction of the recombinant viral particle, refer to FIGS. 7A through 7C, 8A, 8B, and 9A through 9C. The vectors discussed below may be constructed by conventional means and are known and available to those of skill in the art. [See, e.g., Sambrook et al, cited above.]

In one embodiment, a gag/pol expressing cell is constructed by transfection with a gag/pol encoding vector construct. Preferably, the cell line is stable. Suitable constructs and packaging cell lines for retroviruses are well known in the art and are available commercially and from suitable depositories, including the American Type Culture Collection. Preferably by a separate transfection, the host cell is transformed with the vector coemployed in theimeric construct may be employed in the construction.

Figure 7A:
Figure 7B:
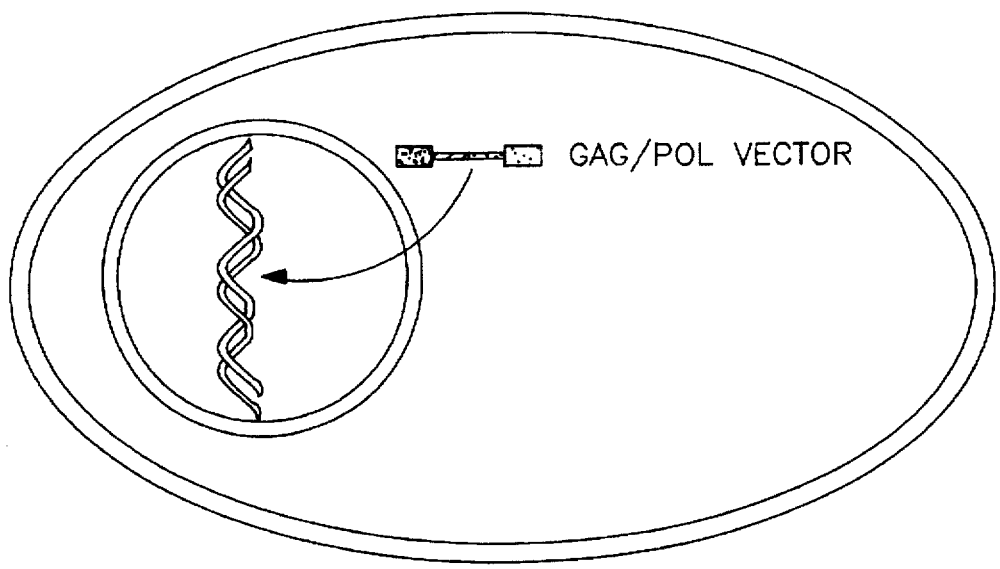
Figure 7C:
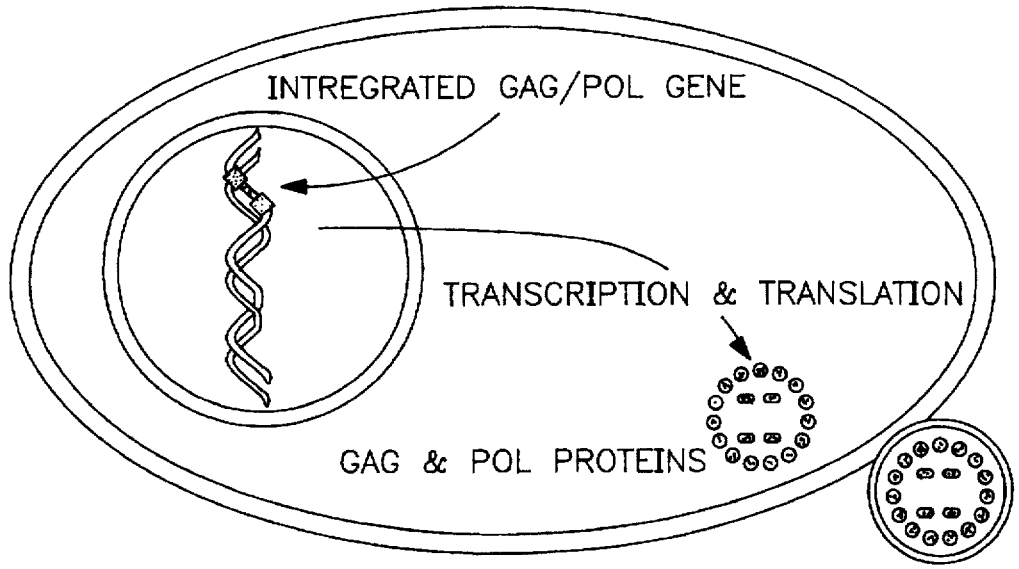

Alternatively, such as in FIGS. 7A through 7C, the vectors containing HIV gag and pol are transfected into the host cell first to produce a gag/pol expressing cell line. Then, as illustrated in FIGS. 8A and 8B, the chimeric construct may be transfected into the gag/pol expressing cell line.

The sequences of the gag and pol genes are readily available from the Genbank and EMBL computer databases and published in *Human Retroviruses and AIDS*, I–II, ed. G. Myer et al (1993). By "functional sequences" is meant either the complete sequences or partial sequences encoding enough of the structural and polymerase genes to produce their respective functions. The functions which these sequences are capable of include directing the production of a viral particle in the mammalian host cell in optional operative association with a conventional packaging sequence, which may be introduced into the host cell.

The chimeric construct and the gag and pol sequences will become chromosomally integrated into the genome of the same host cell, as shown in the above-identified figures. However, extrachromosomal expression will also be useful. Expression of the host cell according to FIG. 8B results in the synthesis of "empty" retroviral particles (i.e. a chimeric envelope containing no viral RNA). Neither the gag/pol construct nor the chimeric envelope construct of the invention contain a retrovital packaging sequence, which is a sequence which on an RNA molecule bind to the gag protein when the viral particle forms. Thus their transcribed RNA molecules are not incorporated into the retroviral particles.

Transcripts derived from this construct are incorporated into the retroviral particle. The resultant recombinant retrovirus is replication incompetent since it contains no retroviral nucleic acid.

It is further preferred for the production of a recombinant retroviral particle of this invention to a targeted cell bearing a selected receptor for therapy or diagnosis of a disease state, that a biological mediator be associated with the viral particle. As depicted in FIGS. 9A through 9C, the biological mediator to be delivered to the target cell, e.g., a gene, is cloned by conventional means into yet another vector. Preferably, the gene to be delivered into the target cell is then placed in a third vector construct which contains the packaging sequence using conventional techniques. The selected gene is modified to be operatively associated with the retroviral packaging sequence by inserting the packaging sequence downstream from the transcription initiation site of the selected gene, so that the packaging sequence is within the mRNA (FIG. 9A).

Suitable packaging systems are well known to those of skill in the art. See, e.g. M. A. Bender et al, *J. Virol.*, 61(5):1639–1646 (May 1987); F. Clavel et al, *J. Virol.*, 64(10):5230–5234 (October 1990); A. Lever et al, *J. Virol.*, 63(9):4085–4087 (September 1989). Alternatively, the packaging system may be one which is suitable for expression of the selected biological mediator to be delivered to a selected target cell.

This vector is then introduced into the stable mammalian host cell bearing the chimeric construct, and gag and pol genes (FIG. 9B). Alternatively, the vectors described above may be co-transfected simultaneously into the host cell.

The resulting host cell (FIG. 9B) is cultured, resulting in the production of a recombinant viral particle which carries the selected biological mediator, the chimeric protein, gag and pol, are selected. Since there is no retroviral nucleic acid in the resulting particle (FIG. 9B), it is replication-incompetent, non-pathogenic, and cannot recombine in vivo in a patient. The chimeric construct of the invention, now incorporated into the recombinant retrovirus, directs the recombinant retrovirus to infect cells bearing the appropriate receptor, but will not infect cells lacking this receptor.

By virtue of the particle containing a chimeric protein of this invention, it is able to target any cell or virus bearing the appropriate receptor and thus deliver to that cell the desired polynucleotide drug (FIG. 9C).

Suitable cells or cell lines for transient or stable expression of the chimeric construct, and resulting recombinant viral particle containing it are mammalian cells, such as Chinese hamster ovary cells (CHO) or 3T3 cells. The selection of suitable mammalian host cells and methods for transformation, culture, amplification, screening and production and purification of the viral particle are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines, are the monkey COS-1 cell line, and the CV-1 cell line. Further exemplary mammalian host cells include particularly primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene.

Other suitable and conventionally available mammalian cell lines include, but are not limited to, HeLa, mouse L-929 cells, 3T3 lines derived from Swiss, Balb-c or NIH mice, BHK or HaK hamster cell lines. Also suitable are insect cells, including baculovirus cells.

Thus, the construction of chimeric proteins of the present invention and use thereof in the construction of non-pathogenic recombinant viral particles which are specifically targeted to cell surface proteins allows the delivery of molecules capable of therapeutic action, including anti-viral agents, with high specificity in vivo or in vitro.

Although the following examples focus primarily on the construction of an exemplary chimeric gp120-CD4 construct of this invention, it should be understood that the teachings of the invention may permit the construction of a chimeric gp120-other ligand construct which will perform in an analogous manner. For example, in another embodiment, the nucleotide sequences encoding the Granulocyte-Macrophage Colony Stimulating Factor (GMCSF) which is a ligand for GMCSF-R receptor (GMCSFr) is employed. GMCSF is central to the development of mature hematopoietic cells of the myeloid lineage. It is expressed on pluripotent stem cells. In the same manner as described above, chimeric HIV envelope proteins are engineered to incorporate the entire mature GMCSF molecule into gp120, thus directing retrovirus packaging cell infection to cells expressing GMCSFr. Other suitable ligand-receptor pairs are described above.

Briefly described, to make an exemplary embodiment of a chimeric construct of this invention, the portion of gp120 gene which encodes the CD4 binding site is replaced with a synthetic or artificial nucleotide sequence encoding a ligand capable of targeting selected receptors on selected target cells. As described below and more specifically in Examples 1 and 2, one exemplary chimeric construct is prepared wherein portions of CD4, the HIV gp120-binding domain, replace the native CD4-binding domain of the gp120. In a preferred embodiment, the chimeric construct comprises a nucleotide sequence encoding gp160, wherein the sequence encoding from about amino acids 392 through about 446, which occurs between two cysteine residues, corresponding to the sequence of the HIV-2 ROD isolate, has been deleted. Inserted in place of this sequence is a selected ligand-encoding sequence, such as CD-4. The resulting chimeric protein no longer targets uninfected T cells, but binds to its receptor on HIV-infected cells and to circulating virus.

The region of CD4 necessary and sufficient for binding HIV envelope has been mapped to a region within the first immunoglobulin-like domain of CD4 using antibody inhibition and mutation analysis. When expressed in eukaryotic cells this region retains high affinity binding to HIV envelope. The CD4 molecule possesses two external disulfide loops, the first loop of which contains the entire gp120 binding domain. Expression of both loops may be desirable in order to preserve high affinity gp120 binding, perhaps as a result of a requirement of both loops for proper folding of the envelope binding domain when produced in some recombinant systems A chimeric construct for use in generating a recombinant viral particle to target cells infected with HIV (and which express HIV antigens, including gp120), contains the nucleotide sequences of CD4 inserted into the gene coding for the gp120 envelope protein in place of the above-described deleted sequence of gp120. One chimeric construct of the present invention therefore involves replacement of the nucleotide sequence encoding the V4 region of gp120 with portions of the nucleotide sequence encoding CD4 sufficient for binding HIV gp120. The novel constructs express epitopes of both proteins. Incorporation of CD4 epitopes into the CD4 binding domain of gp160 has generated chimeric proteins which preserve some functions of native gp160 and eliminate others. The resulting chimeric construct is a gp120 construct which, upon expression, generates a chimeric protein which is incapable of binding its natural ligand CD4 by virtue of the fact that the CD4 binding domain has been deleted. However, this construct expresses the CD4 epitope responsible for binding gp120, and thus the chimeric protein binds native gp120.

Two methods are used for the design and construction of chimeric constructs. In one exemplary design a section of the gp120 nucleotide sequence encoding the V4 loop as well as additional sequence was deleted. In its place a fragment of the nucleotide sequence encoding CD4 containing either the first disulfide loop or the first and second disulfide loop was inserted. In a second and preferred method of construction of the chimeric construct, a cysteine-for-cysteine replacement was performed between gp120 and CD4. In effect the CD4 nucleotide sequence encoding the binding loops of gp120 are replaced with either the nucleotide sequence encoding single gp120 binding loop of CD4 or the first two loops of CD4. In this way, as much as possible of the native loop structure of each protein is preserved in the construct. This construct may thus be characterized by the correct folding and function of each loop.

In the examples, the construction of exemplary chimeric proteins was performed by using a recombinant DNA procedure called gene splicing by Sequence Overlap Extension (SOEing) or, alternatively, Recombinant polymerase chain reaction (PCR). Recombinant PCR allows the creation of recombinant DNA molecules of at least 3 kb in length precisely joined regardless of restriction sites present. This has allowed the creation of genes coding for chimeric proteins without any alterations in sequence except where desired.

This technique is used to construct chimeric constructs encoding chimeric proteins in which the immunoglobulin-like domain containing the CD4 binding domain of HIV-2 gp120 is replaced by regions of CD4 responsible for binding HIV gp120. Chimeric HIV-2 Env-CD4 constructs were created whose junctions are the cysteine residues that define the subunit structure of the native proteins. These cysteine residues are disulfide bonded in the native proteins and domain exchange is performed at these points in the anticipation that cysteine binding patterns might be preserved in the chimeric proteins.

These constructs may then be inserted into an appropriate expression vector and an appropriate host cell transfected therewith for expression of the chimeric envelope proteins. Two such chimeric envelope proteins are described in the following examples: one (ROD Env-1 loop) contains the first cysteine loop of CD4 and the other (ROD Env-2 loop) contains the first two loops of the CD4 molecule in place of the CD4 binding domain of HIV-2 ROD gp120.

These constructs have been expressed in COS cells in a transient assay. These chimeric constructs do not appear to be processed into mature proteins and do not mediate fusion between transfected cells expressing them and CD4+cells. As shown in Example 4, anti-CD4 antibodies fail to precipitate the envelope-CD4 chimera containing the first loop of CD4. Both the region of gp120 replaced and the region of CD4 inserted are of similar size, are involved in receptor-ligand interactions (and thus are exposed on the surface of their native molecules), and are structurally related (insofar as they are members of the immunoglobulin superfamily). It is expected that the CD4 epitope would be preserved in the context of the HIV-2 envelope. The chimeric protein, ROD Env-1 loop, appears to dimerize, as has been described for native HIV-2 gp160.

Surprisingly, however, incorporation of a substantially larger portion of the CD4 molecule is required for the preservation of epitopes necessary for antibody binding. The two loop chimera expresses epitopes of CD4 which are capable of binding native HIV envelope protein, as the chimeric envelope is precipitable by anti-CD4 antibodies in the immunoprecipitation assay described below.

As noted above, expression of both the first two immunoglobulin-like domains of CD4 has previously been observed in some cases to be necessary to retain proper folding. This requirement is confirmed when the HIV envelope binding domain of CD4 is expressed as a part of the viral particle which also contains HIV env sequences.

These chimeric constructs, proteins, transfected cells containing them and the resulting viral particles of this invention have significant use in therapeutic and possibly diagnostic application. For example, a selected ligand nucleotide sequence may be incorporated into the deleted portion of a gp120 gene sequence, and the resulting chimeric construct is used in the production of a recombinant viral particle capable of targeting to a cell or virus bearing the ligand's receptor. Such a viral particle may be produced using conventional techniques as described herein.

Where the viral particle contains a CD4 ligand, a viral particle according to this invention will bind to gp120 on cells infected with HIV. Thus, this embodiment of the technology will have utility in the treatment of HIV infection, as it allows the specific delivery to infected cells of biological mediators which can inhibit HIV spread. Additionally, circulating HIV will be targeted.

Alternatively, where the ligand in the chimeric construct and resulting viral particle is GMCSF, for example, the viral particle will bind to the GMCSF receptor on the stem cells. This embodiment permits the delivery of biological mediators (such as genes) to the pluripotent stem cells to correct blood-born disorders of metabolism or to "intracellularly immunize" lineages of leukocytes against infectious agents such as viruses. For example, the recombinant retrovirus can be engineered to deliver polynucleotide drugs to stem cells.

The viral particles of this invention may also be used to deliver a dominant negative mutant of a viral protein such as gag to a stem cell, which will protect the stem cells and progeny from viral infection [D. Bevac et al, *Proc. Natl. Acad. Sci. USA,* 89:9870–9874 (October 1992), M. H. Malim et al, *J. Exp. Med.,* 176:1197–1201 (October 1992)].

Other ligands in chimeric constructs and resulting viral particles constructed according to this invention will be useful in other therapies and the selection of the ligands and conditions to be treated requires no undue experimentation, merely selection of ligands and diseases based on known information with resort to the teachings herein.

The following examples are illustrative in nature and the disclosure is not limited thereto.

EXAMPLE 1

Gene Construction

Native HIV-2 envelope gene, gp160-rev, was amplified by the PCR technique [see, e.g., H. A. Erlich, ed., "PCR Technology", Stockton Press: New York (1989) and H. A. Erlich et al, (eds), "Polymerase Chain Reaction" in Curr. Comm. Mol. Biol., Cold Spring Harbor Laboratory Press, New York (1989)] from an HIV isolate, HIV-2 ROD, cloned in phage lambda [National Institutes of Health] as follows. The complete molecular clone is referred to as HIV-2 ROD-lambda.

The PCR primers [SEQ ID NO: 3–10], A and H from FIG. 1, were designed to amplify the region of the HIV-2 genome encompassing the rev and env open reading frames and relevant splice sites. The design of these primers was based on the known published sequence of the HIV-2 ROD virus.

The primers were used to amplify a sequence of 2708 base pairs from HIV-2 ROD-lambda, as illustrated in the top third of FIG. 2. The resulting PCR products were cloned into the plasmid pCDNA I/NEO [commercially available from InVitrogen], a vector allowing high expression in a mammalian cell transient assay system (COS), using XhoI (5') and XbaI (3') restriction sequences incorporated into the primers as shown in FIG. 1.

EXAMPLE 2

Construction of Chimeric env-CD4 DNA Constructs by Recombinant PCR

Primers were designed to amplify three DNA fragments to be joined together to construct the final construct.

HIV-2 rev-160 primers of FIG. 1 were used in the PCR technique conducted on the previously amplified 2708 base pair sequence of the HIV-2 rev-envelope gene amplified as described above in a manner illustrated in FIGS. 2A, 2B, and 2C. As illustrated in FIG. 2A, primers A and B [SEQ ID NO: 3 and 4] were used to amplify a fragment of the env gene, corresponding to the first exon of rev and amino acids 1–392 of the HIV-2 gp160; primers G, F and H [SEQ ID NO: 9, 8 and 10] were used to amplify another portion of the rev gene corresponding to amino acids 446–858 of HIV-2 gp160, the second exon of rev. The primers A [SEQ ID NO: 3], B [SEQ ID NO: 4], G [SEQ ID NO: 9], F [SEQ ID NO: 8], and H [SEQ ID NO: 10] of FIG. 1 incorporated approximately 15 base pairs homologous to the CD4 region to be joined so that the resulting PCR products would be readily fused to the CD4 loop sequences. The resulting PCR products of these priming events are illustrated in FIG. 2A as two portions of the env and rev genes respectively, each containing a cross-hatched sticky end for the CD4 loop sequence.

Amplification of these two portions omitted the coding sequence for 54 amino acids of gp160 corresponding to the region between the two cysteines at amino acid numbers 392 and 446.

Referring to FIG. 2B, another priming event was performed using the published CD4 template 4pMV7 and primers C [SEQ ID NO: 5], D [SEQ ID NO: 6], and E [SEQ ID NO: 7] from FIG. 1. These primers were used to amplify the regions of CD4 to be incorporated into the gp160 molecule. These amplified sequences encoded either the first cysteine loop of CD4 (amino acid numbers 16–84 from the published sequence) or the first two loops of CD4 (amino acid numbers 16–159 from the published sequence).

Finally, FIG. 2C depicts the recombination event between these three primary PCR products, i.e., the env and rev sequences with the appropriate CD4 loop structure. To recombine the three primary PCR products, a PCR reaction was performed in which the products to be joined were mixed together with the far 3' and 5' envelope primers A [SEQ ID NO: 3] and H [SEQ ID NO: 10] of FIG. 1. Recombination between the three primary PCR products occurred by virtue of the homologous regions incorporated in the primary PCR reactions and the recombination product was amplified by the external primers. This final product is illustrated by the lower bar graph of FIG. 2C. All products were confirmed to be correct recombinants by restriction analysis.

The two chimeric Env-CD4 constructs created, ROD Env-1 loop and ROD Env-2 loop, retain many characteristics of native HIV-2 gp160, but to varying degrees. Both maintain reactivity with antibodies specific for the HIV-1 envelope, and both maintain interaction with the virus and fusogenicity. They vary by incorporating CD4 sequence and by their reactivity with anti-CD4 antibodies.

The amplified recombinant sequences were subcloned into the XhoI-XbaI sites of pCDNA I/NEO to provide suitable plasmids for transfection.

EXAMPLE 3

Transient Transfection Assay

For transfection, COS-7 (SV40 transformed monkey kidney) cells were grown in DMEM supplemented with 10% fetal calf serum and penicillin and streptomycin. For each assay below, approximately 1×10⁶ COS-7 cells were transfected with approximately 2 μg of double cesium banded DNA by DEAE dextran transfection in the presence of chloroquine. Cells were harvested and/or assays performed at 40–72 hours post transfection. Transfectants were analyzed by immunoprecipitation and by a cell fusion assay described below.

The expression of recombinant chimeric protein in this system yields chimeric HIV-2 envelope protein with the same biological characteristics as observed in virally infected cells.

EXAMPLE 4

Syncytium Assay

To determine whether the amplified env gene of HIV-2 ROD could mediate the fusion of HIV-2 infected cells with uninfected cells, the following assay was conducted. For this assay, Sup-T1, a CD4+ human non-Hodgkins T lymphoma [American Type Culture Collection, Rockville, Md.] was grown in RPMI medium with 10% fetal calf serum (FCS) and penicillin/streptomycin.

The transfected cells of Example 1 were incubated with Sup-T1 cells at day 1 following transfection and examined visually for the formation of multinucleated giant cells (syncytia) at regular intervals until COS cell death caused by the overreplication of plasmid DNA.

The kinetics of fusion with CD4+ cells is faster for HIV-2 envelope-expressing cells than for HIV-1 HXB2 expressing cells (a strain cloned and expressed in a similar manner) [NIH]. This phenomenon reiterates the difference in fusion kinetics observed for infected cells.

This assay demonstrated that the biological function of these cloned HIV chimeric proteins is preserved. This assay may also be employed to demonstrate that the biological function of the env portion of the recombinant construct is also retained.

EXAMPLE 5

Immunoprecipitations

The recombinant chimeric proteins described above are tested in an immunoprecipitation assay with antibodies to the native HIV env and CD4 proteins, to determine if the sequences in the chimeric proteins resemble the native protein, as shown by antibody recognition. For example, the recognition of the HIV env is essential so that the recombinant chimeric protein retains characteristics; necessary for infectivity of target cells specifically, association with virus and fusogenicity are retained. The recognition of the CD4 loop(s) is necessary to determine if the sequence of this ligand retains its ability to bind to its receptor.

A. HIV-2 env-CD4 1 loop.

After about 48 hours, approximately $1\times10^6$ COS-7 cells transfected with 2 μg of the plasmid containing the recombinant chimeric construct containing one CD4 loop and described in Example 3 were metabolically labelled with $^{35}$S-methionine and -cysteine for 4 to 16 hours in a 5% $CO_2$ atmosphere. Cells were solubilized and lysed in standard lysis buffer containing 0.5% Triton-X 100 and 0.5% Deoxycholate.

Chimeric HIV-2 envelope proteins were immunoprecipitated using pig anti-HIV-2 serum [Verigen Corp.], normal pig serum (negative control), a cocktail of anti-CD4 antibodies or an irrelevant monoclonal antibody, bound to protein A agarose. Anti-HIV-2 antibodies were either immune patient serum [NIH AIDS Research Reagent Reference Program (ARRRP)] or the pig serum against HIV-2. Anti-CD4 antibodies used to precipitate chimeric proteins were a mixture of Leu-3a, SIM.2 [ARRRP], SIM.4 [ARRRP], and a R-anti-CD4 polyclonal serum [ARRRP].

Labelled proteins were reduced and then run on 10% SDS-PAGE and autoradiographed. The resulting gel is illustrated in FIG. 3. The chimeric protein containing only one CD4 loop is not precipitable by anti-CD4 antibodies, indicating that the CD4 epitopes are improperly expressed and/or hidden. The ROD Env-1 loop chimeric protein is produced in COS cells as a protein of approximate molecular weight of 98 kd, the predicted molecular weight based on the size and glycosylation patterns of the native subunits. The ROD Env-1 loop chimera oligomerizes to yield a band of approximately 300 kd in the same manner as native HIV-2 gp160. The region(s) of the envelope protein responsible for gp160 oligomerization are not known but the region deleted (a.a. 393–445) does not appear to be required for oligomerization. However, the single loop chimera appears to be cleaved poorly if at all into the transmembrane and external proteins.

B. HIV-2 env-CD4 2 loop.

As described above for part A, approximately $1\times10^6$ COS-7 cells transfected with 2 μg plasmid DNA containing the chimeric construct with two loops of CD4 as the ligand using DEAE-dextran in the presence of chloroquine were, after 48 hours, metabolically labelled with $^{35}$S-methionine and -cysteine for between 4 to 16 hours then solubilized in the above-described lysis buffer. Immunoprecipitation was performed using human anti-HIV-2 serum or the cocktail of anti-CD4 antibodies bound to protein A agarose, described above.

Labelled proteins were reduced, and then run on 10% SDS-PAGE and autoradiographed. The resulting gel is illustrated in FIG. 4. The chimeric protein ROD Env-2 loop is precipitable with anti-CD4 antibodies to reveal a single band at approximate molecular weight 160 kd, the size predicted for an uncleaved chimeric protein. No oligomerization has been observed for the ROD Env-2 loop protein. However, proteins of such high molecular weight are poorly loaded and resolved (note the barely loaded oligomer bands for native gp160) in these gels.

In addition, the yield of the chimeric ROD Env-2 loop protein is substantially lower than for native envelope or for chimeric ROD Env-1 loop protein. Substitution of heterologous leader sequences has been observed to be necessary for high expression of HIV envelopes and mutant proteins in several systems and may be of benefit in this system.

EXAMPLE 6

Construction of a Chimeric Construct with a GMCSF Ligand

In the construction of an HIV env-GMCSF chimeric construct, a section of gp120 that is greater than just the V4 loop is replaced in order to (1) insert the entire mature GMCSF sequence and (2) preserve as much as possible the original size of gp120. Studies have shown that most or all of the GMCSF molecule is required for binding to its receptor. As there is no cysteine for cysteine exchange possible between GMCSF and gp120, preservation of the relative size of the envelope sequence is desired. Additional chimeric constructs of env-GMCSF may also preserve of as much of gp120 as possible.

The following experiments describe the construction of a chimeric protein made according to the invention using a GMCSF nucleotide sequence inserted into the nucleotide sequence encoding the HIV-1 envelope. These experiments also describe the ability of this chimeric protein to infect a selected target cell.

EXAMPLE 7

Construction of HIV/GMCSF Chimeric Protein

The HIV-1/GMCSF chimeric construct was prepared as described in Example 1, with the following exceptions. DNA oligonucleotide sequences used for making HIV-1/GMCSF chimeric envelopes are as follows. The lower case letters indicate HIV1 HXB2 sequence, which is available from GenBank. The plasmid can be obtained from the AIDS Reference Bank Repository. The upper case letters indicate human GM-CSF sequence from G. Wong et al, *Science*, 228:810–815 (1985).

| Primer/SEQ ID Nos. | Primer Sequences |
| --- | --- |
| 6054/11 | XhoI |
| | 5' ccttaagctcgagcctatggcaggaagaagcg |
| 5870/12 | XbaI |
| | 5' cacttgttctagaatcttatagcaaaatcc |
| 5850/13 | 5' ATGCTGCCAGGGCTGgttattccattttgc 3' |
| 5851/14 | 5' gcaaaaatggaataacCAGCCCTGGCAGCAT 3' |
| 5852/15 | 5' ctcttgttaatagcagCTCCTGGACTGGCTC 3' |
| 5853/16 | 5' GAGCCAGTCCAGGAGctgctattaacaagag 3' |

Two HIV-1 envelope fragments were amplified via the PCR using pairs of primers: 6054/5850 [SEQ ID NO: 11 and 13] and 5853/5870 [SEQ ID NO: 16 and 12]. A single human GMCSF fragment was amplified using primers 5851 [SEQ ID NO: 14] and 5852 [SEQ ID NO: 15]. These three PCR DNA fragments were combined in a third PCR reaction containing only primers 6054 [SEQ ID NO: 11] and 5870 [SEQ ID NO: 12]. The product of this second PCR reaction was digested with restriction enzymes XbaI and XhoI, the sites for which (TCTAGA and CTCGAG, respectively) were introduced at the ends of the DNA fragments via the primers, then ligated into the plasmid pCDNAI/neo [InVitrogen] to create 160-GMSCF-pCDNAI/neo.

The sequence of the resulting GMCSF/HIV-1 chimeric construct is provided in FIG. 5 [SEQ ID NO: 1]. The lower case letters indicate the fragments originating from GMCSF and the two restriction endonuclease sites. The rest of the sequence, in upper case letters, is from HIV-1, including the envelope and rev genes.

EXAMPLE 8

Transient Transfection Assay

A. Construction of pNLpuro pNL43 [Adachi et al, *J. Virol.*, 59:284–291 (1986)] consists of HIV1 proviral DNA plus 3 kb of host sequence from the site of integration cloned into pUC18. pNLpuro is described in D. Levy et al, "Induction of Cell-Differentiation by Human Immunodeficiency Virus-1 VPR", *Cell*, 72(4):541–550 (1993) and was constructed as follows.

Briefly, the StuI site within the non-HIV 5' flanking human DNA of pNL43 was destroyed by partial digestion with StuI followed by digestion of the free ends with E. coli polymerase I. The linear plasmid was filled, then self-ligated, leaving a unique StuI site within the HIV genome. This plasmid, pNLΔstu, was then digested with the blunting enzymes StuI and BsaBI, which eliminated a large section of the coding sequence for gp120. The SV40 promoter and puromycin resistance coding region (puromycin acetyltransferase) were isolated from pBABE-puro [Morgenstern and Land, *Nucl. Acids Res.*, 18:3587–3596 (1990)] using EcoRI and ClaI. This fragment was blunted, then cloned into the StuI-BsaBI-digested pNLΔstu. A clone was selected with the SV40-puro fragment in the correct orientation so that the 3' long terminal repeat of HIV could provide poly(A) functions for the puromycin acetyltransferase message. This plasmid was designated pNLpuro.

B. Assay

The 160-GMCSF-pCDNAI/neo envelope deleted chimeric construct prepared as described in Example 7 above, was cotransfected into COS-7 along with the envelope-deletion HIV-1 genomic DNA construct pNLpuro, using the techniques described in Example 3.

Forty-eight hours later, supernatants containing intact retroviral particles were used to infect Sup-T1 cells, as described in Example 4. The cells were then selected in puromycin [5 μg/mL] for three days and photographed. The envelope deleted virus carries the puromycin-resistance gene, so surviving cells indicate successful infection by the recombinant viral particles. Surviving cells are distinguished by their clear round morphology and growth in clusters versus the irregular granular morphology of dead cells.

The results showed that numerous round, clear structures on cells. This indicates the ability of the recombinant chimeric protein to associate with the remainder of the viral particle, resulting in a productive infection. In the positive controls, cells infected with virus containing the HIV-1 (HXB2) native envelope, or cells infected with virus containing the HIV-2 (ROD) native envelope, demonstrate numerous large, round, clear cells, some in clusters.

GM-CSF is similar in size to CD4. In reference to the CD4/envelope chimeric proteins, antibodies against both CD4 and the native envelope recognize the chimeric proteins. This indicates that the structural integrity of each component of the chimeric proteins is maintained and that they are functional. Thus, functionality for the GMCSF/HIV chimeric protein is proven where productive infection occurred.

Further, additional support for the binding of chimeric protein as of the invention is provided by the successful infection of Sup-T1 cells by the HIV-1/GM-CSF chimeric protein, and by the antibody staining of both HIV-1/CD4 and HIV-2/CD4 chimeric proteins and for CD4.

EXAMPLE 9

Construction of HIV-1/CD4 Chimeric Construct

The following experiment describes a chimeric construct formed by the HIV-1 envelope and CD4. The sequence of this chimeric construct is provided in FIG. 6.

The DNA oligonucleotide sequences used for making HIV-1/CD4 chimeric construct are as follows. The lower case letters indicate HIV-1 HXB2 sequence. The upper case letters indicate human CD4 sequence.

| Primer/SEQ ID No. | Primers |
| --- | --- |
| 5868/17 | 5' acaattaaaactgtgcg |
| 4835/18 | 5' cgcacagttttaattgtACAGCTTCCCAGAAGAAG |
| 4834/19 | 5' CCTGTAATATTTGATGAgcatgtccaggtgccac |
| 4888/20 | 5' tcatcaaatattacagg |

Two HIV-1 envelope fragments were amplified using primers 6054 [SEQ ID NO: 11] and 5868 [SEQ ID NO: 17]; a single CD4 fragment was amplified using primers 4835 [SEQ ID NO: 18] and 4834 [SEQ ID NO: 19]. The three resulting PCR amplified DNA fragments were combined in a PCR reaction with primers 6054 [SEQ ID NO: 11] and 5870 [SEQ ID NO: 12], as in the env/GMCSF construct. The resulting PCR product was subcloned, as described above in Example 7, into pCDNA/neo [InVitrogen] to yield the plasmid vector, HIV-1 160-CD4-pCDNAI/neo.

COS-7 cells were transfected with HIV-1 160-CD4-pCDNAI/neo or 160-GMCSF-pCDNAI/neo. Two days later chimeric proteins from the cells were analyzed in Western blot as described in Example 5 with the exception that antibodies with specificity for HIV-1 proteins were used in place of antibodies with specificity for HIV-2. Antibody staining provided support for the binding of these chimeric proteins.

EXAMPLE 10

Construction of Recombinant Retroviral Particle

A desired host cell is either transiently or stably co-transfected with multiple expression vectors. In a preferred method, three vectors are used. One vector encodes a modified chimeric envelope construct prepared according to the invention. See, FIG. 7B and Examples 2, 7 and 9. A second vector includes a gag/pol expression cassette. See FIG. 7A. (See, e.g., pNLpuro, described in Example 8 above). Neither of these vectors includes the prototypic packing signal for the expressed message termed ψ (psi). A third vector includes the ψ signal as well as the therapeutic gene to be delivered upon co-transfection, into a cell. See FIG. 7C. Gag and pol proteins are produced along with the engineered env protein and message RNA from all three expression cassettes. Gag and pol and the env proteins as well as the single message containing the ψ signal aggregate and give rise to novel viral particles, which now target to a novel receptor and deliver the therapeutic gene "attached" to the ψ signal.

EXAMPLE 11

Method of Using Recombinant Retroviral Particle

A recombinant virus is constructed, as described above in Example 10, to specifically target GM-CSF receptor bearing cells and to deliver the gene for herpes thymidine kinase (TK) to a mixture of cells, some of which bear GM-CSF receptors and some of which do not. Following infection, the cells are grown in selective media containing hypoxanthine, aminopterin and thymidine (HAT media). Only cells containing the GM-CSF receptor prior to infection and selection will reveal lower receptor expression compared with those cells infected and selected in HAT media. Treatment of the TK-expressing cells with gangcyclovir targets the TK bearing cells for destruction, resulting in widespread cell death.

Numerous modifications and variations of the present invention are included in the above-identified specification and are expected to be obvious to one of skill in the art. For example, use of other appropriate receptor-ligand systems than CD4-gp120 can be employed and selected retroviruses other than HIV-1 and HIV-2 are contemplated in the performance of this invention. Such modifications and alterations to the compositions and processes of the present invention are believed to be encompassed in the scope of the claims appended hereto.

What is claimed is:

1. A chimeric nucleotide construct comprising an HIV gp160 envelope gene from which the sequence encoding about amino acid 392 to about amino acid 446 or a fragment thereof corresponding to the HIV binding site to CD4 has been deleted and into which has been inserted a heterologous sequence encoding a ligand, said ligand selected from the group consisting of GMCSF and CD4.

2. The construct according to claim 1 wherein said HIV is selected from the group consisting of HIV-1 and HIV-2.

3. The construct according to claim 2 wherein said HIV-2 is the isolate HIV-2 ROD.

4. A chimeric nucleotide construct SEQ ID NO:1.

5. A chimeric nucleotide construct SEQ ID NO:2.

6. A vector comprising:

a chimeric nucleotide construct comprising an HIV gp160 envelope gene from which the sequence encoding about amino acid 392 to about amino acid 446 or a fragment thereof corresponding to the HIV binding site to CD4 has been deleted and into which has been inserted a heterologous sequence encoding a ligand selected from the group consisting of GMCSF and CD4; and a regulatory sequence which directs expression of the chimeric construct.

7. A host cell transformed with the vector of claim 6.

8. A method for producing a chimeric protein comprising culturing a host cell according to claim 7 and recovering the expressed chimeric protein.

9. A recombinant retroviral particle comprising:

(a) a chimeric protein comprising an HIV gp160 envelope from which about amino acid 392 to about amino acid 446 or a fragment thereof corresponding to the HIV binding site to CD4 has been deleted and into which has been inserted a heterologous sequence encoding a ligand selected from the group consisting of GMCSF and CD4;

(b) a biological mediator gene sequence for delivery to the target cell;

(c) a retroviral gag protein;

(d) a retroviral pol protein; wherein the particle lacks HIV nucleic acid, rendering it non-pathogenic and incapable of recombination.

10. The retroviral particle according to claim 9 wherein the mediator is selected from the group consisting of a gene product, a diagnostic label, and a toxic agent.

11. A host cell transformed with the vector of claim 6, wherein said cell further comprises:

(a) a gene encoding a biological mediator selected from the group consisting of a gene product and a toxic agent;

(b) a retrovital packaging sequence; and (c) a retrovital gag gene and a retrovital pol gene in operative association with regulatory sequences capable of directing the replication and expression thereof.

\* \* \* \* \*